(12) United States Patent
Awad et al.

(10) Patent No.: US 8,632,797 B2
(45) Date of Patent: Jan. 21, 2014

(54) TARGETED DELIVERY OF THERAPEUTIC AGENTS WITH LYOPHILIZED MATRICES

(75) Inventors: Hani A. Awad, Rochester, NY (US); Edward M. Schwarz, Rochester, NY (US)

(73) Assignee: University of Rochester, Rochester, NY (US)

( * ) Notice: Subject to any disclaimer, the term of this patent is extended or adjusted under 35 U.S.C. 154(b) by 718 days.

(21) Appl. No.: 12/513,161

(22) PCT Filed: Oct. 31, 2007

(86) PCT No.: PCT/US2007/083219
§ 371 (c)(1),
(2), (4) Date: Feb. 8, 2010

(87) PCT Pub. No.: WO2008/063839
PCT Pub. Date: May 29, 2008

(65) Prior Publication Data
US 2012/0093801 A1   Apr. 19, 2012
US 2012/0251522 A2   Oct. 4, 2012

Related U.S. Application Data

(60) Provisional application No. 60/855,774, filed on Oct. 31, 2006, provisional application No. 60/855,941, filed on Nov. 1, 2006.

(51) Int. Cl.
*A61K 9/14*        (2006.01)
*A61K 48/00*       (2006.01)
*C07H 21/02*       (2006.01)
*C12N 15/00*       (2006.01)

(52) U.S. Cl.
USPC .......... 424/425; 424/484; 424/93.2; 536/23.5

(58) Field of Classification Search
USPC .................. 424/425, 484, 93.2; 536/23.5
See application file for complete search history.

(56) References Cited

U.S. PATENT DOCUMENTS

| | | | |
|---|---|---|---|
| 5,707,962 A | | 1/1998 | Chen et al. |
| 5,801,014 A | | 9/1998 | Lee et al. |
| 5,962,427 A | * | 10/1999 | Goldstein et al. ............ 514/44 R |
| 5,986,058 A | | 11/1999 | Lee et al. |
| 5,994,094 A | * | 11/1999 | Hotten et al. ................ 435/69.1 |
| 6,090,563 A | | 7/2000 | Lee et al. |
| 6,764,994 B1 | | 7/2004 | Hoetten et al. |
| 6,894,022 B1 | | 5/2005 | Hubbell et al. |
| 2003/0049299 A1 | | 3/2003 | Malaviya et al. |
| 2003/0143207 A1 | | 7/2003 | Livesey et al. |
| 2004/0009155 A1 | | 1/2004 | Palasis et al. |
| 2004/0062592 A1 | * | 4/2004 | Shekalim et al. ............. 401/208 |
| 2005/0043813 A1 | | 2/2005 | Kusanagi et al. |
| 2006/0204441 A1 | | 9/2006 | Atala et al. |
| 2007/0248575 A1 | * | 10/2007 | Connor et al. ................ 424/93.7 |
| 2008/0199443 A1 | * | 8/2008 | Moos et al. .................. 424/93.21 |
| 2008/0274184 A1 | * | 11/2008 | Hunt ............................ 424/484 |

FOREIGN PATENT DOCUMENTS

EP           1604694        12/2005
WO   WO 2007/0109180        9/2007

OTHER PUBLICATIONS

Basile P. et al. Freeze-dried tendon allografts as tissue-engineering scaffolds for Gdf5 gene delivery. Mol. Ther. 16:466-473, 2008.*
Abrahamsson, S.O., Gelberman, R.H., Amiel, D., Winterton, P. & Harwood, F. (1995) *J. Orthop. Res.* 13: 58-66.
Abrahamsson, S.O. & Lohmander, S. (1996) *J. Orthop. Res.* 14: 370-6.
Ark, J.W., Gelberman, R.H., Abrahamsson, S.O., Seiler, J.G., 3rd & Amiel, D. (1994) *J. Hand. Surg. [Am]* 19: 249-58.
Asencio, G., Abihaidar, G. & Leonardi, C. (1996) *J. Hand Surg. [Br]* 21: 84-8.
Aspenberg, P. & Forslund, C. (1999) *Acta. Orthop. Scand.* 70: 51-4.
Awad, H.A., Boivin, G.P., Dressler, M.R., Smith, F.N., Young, R.G. & Butler, D.L. (2003) *J. Orthop. Res.* 21: 420-31.
Awad, H.A., Butler, D.L., Boivin, G.P., Smith, F.N., Malaviya, P., Huibregtse, B. & Caplan, A.I. (1999) *Tiss. Eng.* 5: 267-77.
Banes, A.J., Tsuzaki, M., Hu, P., Brigman, B., Brown, T., Almekinders, L., Lawrence, W.T. & Fischer, T. (1995) *J. Biomech.* 28: 1505-13.
Bechtold, J.E., Eastlund, D.T., Butts, M.K., Lagerborg, D.F. & Kyle, R.F. (1994) *Am. J. Sports Med.* 22: 562-6.
Beris, A.E., Darlis, N.A., Korompilias, A.V., Vekris, M.D., Mitsionis, G.I. & Soucacos, P.N. (2003) *J. Hand Surg. [Am]* 28: 652-60.
Bowden, B.W. (1974) *J. Am. Osteo. Ass'n* 74: 144-7.
Bright, R.W. & Green, W.T.: (1981) *J. Pediatr. Orthop.* 1: 13-22.
Bunnell, S. (1953) *Ind. Med. Surg.* 22: 251-4.
Chang, J., Thunder, R., Most, D., Longaker, M.T. & Lineaweaver, W.C.: (2000) *Plast. Reconstr. Surg.* 105: 148-55.
Chen, Y., Luk, K.D., Cheung, K.M., Xu, R., Lin, M.C., Lu, W.W., Leong, J.C. & Kung, H.F.: (2003) *Gene Ther.* 10: 1345-53.

(Continued)

*Primary Examiner* — Quang Nguyen
(74) *Attorney, Agent, or Firm* — James W. Hill; McDermott Will & Emery LLP

(57) ABSTRACT

Embodiments of surgical grafts, and methods, for the delivery of therapeutic agents to a target tissue via acellular matrices, are described. In some embodiments, nonviable matrices are successful in preventing or lessening adhesion formation by guiding tissue repair and remodeling, while also providing the target tissue with therapeutic agents that can act as repair and remodeling factors. An exemplary method to modulate flexor tendon healing and provide elimination or reduction of fibrotic adhesions involves loading a freeze-dried flexor digitorum longus allograft with recombinant adeno-associated viral (rAAV) vectors for the targeted and transient expression of growth/differentiation factor 5 (GDF5).

12 Claims, 24 Drawing Sheets

(56) References Cited

OTHER PUBLICATIONS

Chhabra, A., Tsou, D., Clark, R.T., Gaschen, V., Hunziker, E.B. & Mikic, B. (2003) *J. Orthop. Res.* 21: 826-35.
Chow, S.P., Hooper, G. & Chan, C.W. (1983) *Hand* 15: 136-42.
Clark, R.T., Johnson, T.L., Schalet, B.J., Davis, L., Gaschen, V., Hunziker, E.B., Oldberg, A. & Mikic, B. (2001) *Connect. Tissue Res.* 42: 175-86.
Cole, D.W., Ginn, T.A., Chen, G.J., Smith, B.P., Curl, W.W., Martin, D.F. & Poehling, G.G. (2005) *Arthro.* 21: 786-90.
Coyle, M.P., Jr., Leddy, T.P. & Leddy, J.P. (2002) *J. Hand Surg.* [*Am*] 27: 581-5.
Duffy, F.J., Seiler, J.G., Hergrueter, C.A., Kandel, J. & Gelberman, R.H. (1992) *J. Hand Surg.* [*Br*] 17: 275-7.
Eming, S.A., Krieg, T. & Davidson, J.M. (2004) *Expert Opin. Biol. Ther.* 4: 1373-86.
Gelberman, R.H. & Manske, P.R. (1985) *Hand Clin.* 1: 35-42.
Gelberman, R.H., Seiler, J.G., 3rd, Rosenberg, A.E., Heyman, P. & Amiel, D. (1992) *Scand J. Plast. Reconstr. Surg Hand Surg.* 26: 257-64.
Gerich, T.G., Kang, R., Fu, F.H., Robbins, P.D. & Evans, C.H. (1996) *Gene Ther.* 3: 1089-93.
Gerich, T.G., Kang, R., Fu, F.H., Robbins, P.D. & Evans, C.H. (1997a) *Knee Surg. Sports Traumatol. Arthrosc.* 5: 118-23.
Gerich, T.G., Lobenhoffer, H.P., Fu, F.H., Robbins, P.D. & Evans, C.H. (1997b) *Unfallchirurg.* 100: 354-62.
Grieger, J.C., & Samulski, R.J. (2005) *Adv. Bioch. Eng. Biotechnol.* 99: 119-145.
Hsu, C. & Chang, J. (2004) *J. Hand Surg.* [*Am*] 29: 551-63.
Indelicato, P.A., Bittar, E.S., Prevot, T.J., Woods, G.A., Branch, T.P. & Huegel, M. (1990) *Am. J. of Sports Med.* 18: 335-42.
Ito, H., Koefoed, M., Tiyapatanaputi, P., Gromov, K., Goater, J.J., Carmouche, J., Zhang, X., Rubery, P.T., Rabinowitz, J., Samulski, R.J., Nakamura, T., Soballe, K., O'Keefe, R.J., Boyce, B.F. & Schwarz, E.M. (2005) *Nat'l Med.* 11: 291-7.
Jackson, D.W., Grood, E.S., Goldstein, J.D., Rosen, M.A., Kurzweil, P.R., Cummings, J.F. & Simon, T.M. (1993) *Am. J. of Sports Med.* 21: 176-85.
Jackson, D.W., Halbrecht, J., Proctor, C., Van Sickle, D. & Simon, T.M. (1996) *J. Orthop. Res.* 14: 255-64.
Jackson, D.W., Windler, G.E. & Simon, T.M. (1990) *Am. J. Sports Med.* 18: 1-10.
Jorgensen, H.G., McLellan, S.D., Crossan, J.F. & Curtis, A.S. (2005) *Cyto.* 30: 195-202.
Kashiwagi, K., Mochizuki, Y., Yasunaga, Y., Ishida, O., Deie, M. & Ochi, M. (2004) *Scand. J. Plast. Reconstr. Surg. Hand Surg.* 38: 193-7.
Khan, U., Edwards, J.C. & McGrouther, D.A. (1996) *J. Hand Surg.* [*Br*] 21: 813-20.
Khan, U., Kakar, S., Akali, A., Bentley, G. & McGrouther, D.A. (2000) *J. Bone Joint Surg. Br.* 82: 1054-8.
Koefoed, M., Ito, H., Gromov, K., Reynolds, D.G., Awad, H.A., Rubery, P.T., Ulrich-Vinther, M., Soballe, K., Guldberg, R.E., Lin, A.S., O'Keefe, R.J., Zhang, X. & Schwarz, E.M. (2005) *Mol. Ther.* 12: 212-8.
Lee, S.J., & Nathans, D. (1988) *J. Biol. Chem.* 263: 3521-3527.
Leversedge, F.J., Zelouf, D., Williams, C., Gelberman, R.H. & Seiler, J.G., 3rd (2000) *J. Hand. Surg.* [*Am*] 25: 721-30.
Lindsay, W.K., Thomson, H.G. & Walker, F.G.: (1960) *Br. J. Plsat. Surg.* 3: 1-9.
Lister, G. (1985) *Hand Clin.* 1: 133-46.
Lin, T.K. & Yang, R.S. (1997) *J. Trauma* 43: 103-6.
Lou, J., Tu, Y., Burns, M., Silva, M.J. & Manske, P. (2001) *J. Orthop. Res.* 19: 1199-202.
Lundborg, G. (1976) *Hand* 8: 235-8.
Lundborg, G., Hansson, H.A., Rank. F. & Rydevik, B. (1980) *J. Hand Surg.* [*Am*] 5: 451-61.
Lundborg, G. & Rank, F. (1978) *J. Hand Surg.* [*Am*] 3: 21-31.
Lundborg, G. & Rank, F. (1980) *Hand* 12: 3-11.
Lundborg, G., Rank, F. & Heinau, B. (1985) *Scand J. Plast. Reconstr. Surg.* 19: 113-7.

Manske, P.R., Gelberman, R.H. & Lesker, P.A. (1985a) *Hand Clin.* 1: 25-34.
Manske, P.R., Gelberman, R.H., Vande Berg, J.S. & Lesker, P.A. (1984) *J. Bone Jt. Surg.* [*Am*] 66: 385-96.
Manske, P.R., Lesker, P.A., Gelberman, R.H. & Rucinsky, T.E. (1985b) *J. Hand Surg.* [*Am*] 10: 632-7.
Masada, K., Yasuda, M., Hashimoto, H. & Nakai, K. (2002) *Scand. J. Plast. Reconstr. Surg. Hand. Surg.* 36: 243-4.
Mehta, V., Kang, Q., Luo, J., He, T.C., Haydon, R.C. & Mass, D.P. (2005) *J. Hand Surg.* [*Am*] 30: 136-41.
Mikic, B. (2004) *Ann. Biomed. Eng.* 32: 466-76.
Mikic, B., Bierwert, L. & Tsou, D. (2006) *J. Orthop. Res.* 24; 831-41.
Mikic, B., Schalet, B.J., Clark, R.T., Gaschen, V. & Hunziker, E.B. (2001) *J. Orthop. Res.* 19: 365-71.
Morotome, Y., Goseki-Sone, M., Ishikawa, I. & Oida, S. (1998) *Biochem. Biophys. Res. Commun.* 244: 85-90.
Morrison, W.A. & Cleland, H. (1995) *Ann. Acad. Med. Sing.* 24: 26-31.
Naam, N.H. (1997) *J. Hand Surg.* [*Am*] 22: 323-7.
Nakamura, T., Yamamoto, M., Tamura, M. & Izumi, Y. (2003) *J. Perio. Res.* 38: 597-605.
Nasca, R.J. (1988) *Clin. Orthop. & Rel. Res.* 228: 218-26.
Poetnza, A.D. & Herte, M.C. (1982) *J. Hand Surg.* [*Am*] 7: 196-9.
Ramesh, R., Kumar, N., Sharma, A.K., Maiti, S.K., Kumar, S. & Charan, K. (2003a) *J. Vet. Med.—Ser. A* 50: 520-6.
Ramesh, R., Kumar, N., Sharma, A.K., Maiti, S.K. & Singh, G.R. (2003b) *J. Vet. Med.—Ser. A* 50: 511-9.
Rickert, M., Jung, M., Adiyaman, M., Richter, W. & Simank, H.G. (2001) *Growth Fact* 19: 115-26.
Rickert, M., Wang, H., Wieloch, P., Lorenz, H., Steck, E., Sabo, D. & Richter, W. (2005) *Connect. Tiss. Res.* 46: 175-83.
Roberts, T.S., Drez, D., Jr., McCarthy, W. & Paine, R.: [*erratum appears in* (1991) *Am. J. Sports Med.* May-Jun.;19(3):272]. (1991) *Am. J. of Sports Med.* 19: 35-41.
Sakellarides, H.T. & Papadopoulos, G. (1996) *J. Hand Surg.* [*Br*] 21: 63-6.
Schneider, L.H. (1985) *Hand Clin.* 1: 109-20.
Seiler, J.G., 3rd, Chu, C.R., Amiel, D., Woo, S.L. & Gelberman, R.H. (1997) *Clin. Orthop. Relat. Res* 345: 239-47.
Seiler, J.G., 3rd, Gelberman, R.H., Williams, C.S., Woo, S.L., Dickersin, G.R., Sofranko, R., Chu, C.R. & Rosenberg, A.E. (1993) *J. Bone Jt Surg.* [*Am*] 75: 1004-14.
Seemann, P., Schwappacher, R., Kjaer, K.W., Krakow, D., Lehmann, K., Dawson, K., Stricker, S., Pohl, J., Ploger, F., Staub, E., Nickel, J., Sebald, W., Knaus, P., & Mundlos, S. (2005) *J. Clin Invest.* 115: 2373-2381.
Sena, K., Morotome, Y., Baba, O., Terashima, T., Takano, Y. & Ishikawa, I. (2003) *J. Dent. Res.* 82: 166-71.
Singer, D.I., Morrison, W.A., Gumley, G.J., O'Brien, B.M., Mitchell, G.M., Barton, R.M. & Frykman, G.K. (1989) *J. Hand Surg.* [*Am*] 14: 55-63.
Slade, J.F., Bhargava, M., Barrie, K.A., Shenbagamurthi, D. & Wolfe, S.W. (2001) *J. Hand Surg.* [*Am*] 26: 813-20.
Smith, P., Jones, M. & Grobbelaar, A. (2004) *Scand. J. Plast. Reconstr. Surg. Hand Surg.* 38: 220-7.
Soslowsky, L.J., Thomopoulos, S., Tun, S., Flanagan, C.L., Keefer, C.C., Mastaw, J. & Carpenter, J.E. (2000) *J. Shoul. Elb. Surg.* 9: 79-84.
Stark, H.H., Anderson, D.R., Zemel, N.P., Boyes, J.H., Ashworth, C.R. & Rickard, T.A. (1989) *Clin. Orthop. Relat. Res.* 242: 51-9.
Tang, J.B., Zhang, Q.G. & Ishii, S. (1993) *J. Hand Surg.* [*Br*] 18: 31-2.
Taras, J.S. & Kaufmann, R.A. (2005) Operative Hand Surgery, 5th Ed., Green, D.P. ed., pp. 241-276.
Taras, J.S. & Lamb, M.J. (1999) *J. Hand Ther.* 12: 141-8.
Tolat, A.R. & Stanley, J.K. (1993) *J Hand Surg.* [*Br*] 18: 239-40.
Toritsuka, Y., Shino, K., Horibe, S., Nakamura, N., Matsumoto, N. & Ochi, T. (1997) *J. Orthop. Res.* 15: 294-300.
Valenti, P. & Gilbert, A. (2000) *Hand Clin.* 16: 573-8.
Vermeylen, J. & Monballiu, G. (1991) *J. Hand Surg.* [*Br*] 16: 185-6.
Wainer, R.A., Clarke, T.J. & Poehling, G.G. (1988) *Arthro.* 4: 199-205.

(56) References Cited

OTHER PUBLICATIONS

Wehbe, M.A., Mawr, B., Hunter, J.M., Schneider, L.H. & Goodwyn, B.L. (1986) *J. Bone Jt. Surg.* [*Am*] 68: 752-63.
Wojciak, B. & Crossan, J.F. (1993) *Clin. Exp. Immunol.* 93: 108-14.
Wolfman, N.M., Hattersley, G., Cox, K., Celeste, A.J., Nelson, R., Yamaji, N., Dube, J.L., DiBlasio-Smith, E., Nove, J., Song, J.J., Wozney, J.M. & Rosen, V. (1997) *J. Clin. Invest.* 100: 321-30.
Wu, Y., Hu, Y. & Cui, S. (2000) *Chin. J. Traumatol.* 3: 34-38.
A. Kanematsu, et al., "Collagenous matrices as release carriers of exogenous growth factors", Biomaterials, Elsevier Science Publishers BV, Barking, GB, vol. 25, No. 18, Aug. 1, 2004, pp. 4513-4520.
Wu, Y., Hu. Y. & Cui. S. (2000) *Chin. J Traumatol.* 3: 34-38.
Radu, et al., Modeling of Drug Release from Collagen Matrices, Journal of Pharmaceutical Sciences, Apr. 2002, vol. 91, No. 4, pp. 964-972.

\* cited by examiner

A

B

C

D

A B C

E

RT-PCR 1. pUC19
2. pSPORT6-*Gdf5*
3. pAAV-*Gdf5*
4. Positive Control

Western Blot 13.7 kDa

1. LacZ-rAAV 1 µl
2. LacZ-rAAV 5 µl
3. LacZ-rAAV 10 µl
4. GDF-5-rAAV 1 µl
5. GDF-5-rAAV 5 µl
6. GDF-5-rAAV 10 µl
7. rmGDF-5 10 ng

A

B

C

D

US 8,632,797 B2

SEQUENCE LISTING

```
<160> NUMBER OF SEQ ID NOS: 2

<210> SEQ ID NO 1
<211> LENGTH: 2643
<212> TYPE: DNA
<213> ORGANISM: Homo sapiens
<220> FEATURE:
<221> NAME/KEY: CDS
<222> LOCATION: (505)..(2007)

<400> SEQUENCE: 1
cgctgccact ggttagcgat aatactggca gcgcgaccgg tttctgaggg ttgttcacct      60
tgctgctcag acgctccgag aagcttcagg cagcataaca cttacagtag agacagggtt     120
tcaccatgtt agccaggatg gtcttgatct cctgacctcg tgatccacct gcctcggcct     180
cccaaggtgc tgggattgca ggcgtgagcc actgcgcctg gccgcaattt acttcattga     240
atctccaaca agagtcctgt gagctgctga ctggagacgt tgcacgtctg gatacgagag     300
catttccact atgggactgg atacaaacac acacccggca gacttcaaga gtctcagact     360
gaggagaaag cctttccttc tgctgctact gctgctgccg ctgcttttga aagtccactc     420
ctttcatggt ttttcctgcc aaaccagagg cacctttgct gctgccgctg ttctctttgg     480
tgtcattcag cggctggcca gagg atg aga ctc ccc aaa ctc ctc act ttc        531
                           Met Arg Leu Pro Lys Leu Leu Thr Phe
                             1               5 ttg ctt tgg tac ctg gct tgg ctg gac ctg gaa ttc atc tgc act gtg       579
Leu Leu Trp Tyr Leu Ala Trp Leu Asp Leu Glu Phe Ile Cys Thr Val
 10              15                  20                  25 ttg ggt gcc cct gac ttg ggc cag aga ccc cag ggg acc agg cca gga       627
Leu Gly Ala Pro Asp Leu Gly Gln Arg Pro Gln Gly Thr Arg Pro Gly
             30                  35                  40 ttg gcc aaa gca gag gcc aag gag agg ccc ccc ctg gcc cgg aac gtc       675
Leu Ala Lys Ala Glu Ala Lys Glu Arg Pro Pro Leu Ala Arg Asn Val
         45                  50                  55 ttc agg cca ggg ggt cac agc tat ggt ggg ggc gcc acc aat gcc aat       723
Phe Arg Pro Gly Gly His Ser Tyr Gly Gly Gly Ala Thr Asn Ala Asn
     60                  65                  70 gcc agg gca aag gga ggc acc ggg cag aca gga ggc ctg aca cag ccc       771
Ala Arg Ala Lys Gly Gly Thr Gly Gln Thr Gly Gly Leu Thr Gln Pro
 75                  80                  85 aag aag gat gaa ccc aaa aag ctg ccc ccc aga ccg ggc ggc cct gaa       819
Lys Lys Asp Glu Pro Lys Lys Leu Pro Pro Arg Pro Gly Gly Pro Glu
```

-continued

```
             90                   95                  100                 105
ccc aag cca gga cac cct ccc caa aca agg cag gct aca gcc cgg act        867
Pro Lys Pro Gly His Pro Pro Gln Thr Arg Gln Ala Thr Ala Arg Thr
                        110                 115                 120 gtg acc cca aaa gga cag ctt ccc gga ggc aag gca ccc cca aaa gca        915
Val Thr Pro Lys Gly Gln Leu Pro Gly Gly Lys Ala Pro Pro Lys Ala
                125                 130                 135 gga tct gtc ccc agc tcc ttc ctg ctg aag aag gcc agg gag ccc ggg        963
Gly Ser Val Pro Ser Ser Phe Leu Leu Lys Lys Ala Arg Glu Pro Gly
            140                 145                 150 ccc cca cga gag ccc aag gag ccg ttt cgc cca ccc atc aca ccc           1011
Pro Pro Arg Glu Pro Lys Glu Pro Phe Arg Pro Pro Ile Thr Pro
        155                 160                 165 cac gag tac atg ctc tcg ctg tac agg acg ctg tcc gat gct gac aga       1059
His Glu Tyr Met Leu Ser Leu Tyr Arg Thr Leu Ser Asp Ala Asp Arg
170                 175                 180                 185 aag gga ggc aac agc agc gtg aag ttg gag gct ggc ctg gcc aac acc       1107
Lys Gly Gly Asn Ser Ser Val Lys Leu Glu Ala Gly Leu Ala Asn Thr
                190                 195                 200 atc acc agc ttt att gac aaa ggg caa gat gac cga ggt ccc gtg gtc       1155
Ile Thr Ser Phe Ile Asp Lys Gly Gln Asp Asp Arg Gly Pro Val Val
            205                 210                 215 agg aag cag agg tac gtg ttt gac att agt gcc ctg gag aag gat ggg       1203
Arg Lys Gln Arg Tyr Val Phe Asp Ile Ser Ala Leu Glu Lys Asp Gly
        220                 225                 230 ctg ctg ggg gcc gag ctg cgg atc ttg cgg aag aag ccc tcg gac acg       1251
Leu Leu Gly Ala Glu Leu Arg Ile Leu Arg Lys Lys Pro Ser Asp Thr
    235                 240                 245 gcc aag cca gcg gcc ccc gga ggc ggg cgg gct gcc cag ctg aag ctg       1299
Ala Lys Pro Ala Ala Pro Gly Gly Gly Arg Ala Ala Gln Leu Lys Leu
250                 255                 260                 265 tcc agc tgc ccc agc ggc cgg cag ccg gcc tcc ttg ctg gat gtg cgc       1347
Ser Ser Cys Pro Ser Gly Arg Gln Pro Ala Ser Leu Leu Asp Val Arg
                270                 275                 280 tcc gtg cca ggc ctg gac gga tct ggc tgg gag gtg ttc gac atc tgg       1395
Ser Val Pro Gly Leu Asp Gly Ser Gly Trp Glu Val Phe Asp Ile Trp
            285                 290                 295 aag ctc ttc cga aac ttt aag aac tcg gcc cag ctg tgc ctg gag ctg       1443
Lys Leu Phe Arg Asn Phe Lys Asn Ser Ala Gln Leu Cys Leu Glu Leu
        300                 305                 310 gag gcc tgg gaa cgg ggc agg gcc gtg gac ctc cgt ggc ctg ggc ttc       1491
Glu Ala Trp Glu Arg Gly Arg Ala Val Asp Leu Arg Gly Leu Gly Phe
    315                 320                 325 gac cgc gcc gcc cgg cag gtc cac gag aag gcc ctg ttc ctg gtg ttt       1539
Asp Arg Ala Ala Arg Gln Val His Glu Lys Ala Leu Phe Leu Val Phe
330                 335                 340                 345 ggc cgc acc aag aaa cgg gac ctg ttc ttt aat gag att aag gcc cgc       1587
Gly Arg Thr Lys Lys Arg Asp Leu Phe Phe Asn Glu Ile Lys Ala Arg
                350                 355                 360 tct ggc cag gac gat aag acc gtg tat gag tac ctg ttc agc cag cgg       1635
Ser Gly Gln Asp Asp Lys Thr Val Tyr Glu Tyr Leu Phe Ser Gln Arg
            365                 370                 375 cga aaa cgg cgg gcc cca ctg gcc act cgc cag ggc aag cga ccc agc       1683
Arg Lys Arg Arg Ala Pro Leu Ala Thr Arg Gln Gly Lys Arg Pro Ser
        380                 385                 390 aag aac ctt aag gct cgc tgc agt cgg aag gca ctg cat gtc aac ttc       1731
Lys Asn Leu Lys Ala Arg Cys Ser Arg Lys Ala Leu His Val Asn Phe
    395                 400                 405 aag gac atg ggc tgg gac gac tgg atc atc gca ccc ctt gag tac gag       1779
Lys Asp Met Gly Trp Asp Asp Trp Ile Ile Ala Pro Leu Glu Tyr Glu
```

-continued

```
                410                 415                 420                 425
gct ttc cac tgc gag ggg ctg tgc gag ttc cca ttg cgc tcc cac ctg          1827
Ala Phe His Cys Glu Gly Leu Cys Glu Phe Pro Leu Arg Ser His Leu
                430                             435                 440 gag ccc acg aat cat gca gtc atc cag acc ctg atg aac tcc atg gac          1875
Glu Pro Thr Asn His Ala Val Ile Gln Thr Leu Met Asn Ser Met Asp
                445                             450                 455 ccc gag tcc aca cca ccc acc tgc tgt gtt ccc acg cgg ctg agt ccc          1923
Pro Glu Ser Thr Pro Pro Thr Cys Cys Val Pro Thr Arg Leu Ser Pro
                460                             465                 470 atc agc atc ctc ttc att gac tct gcc aac aac gtg gtg tat aag cag          1971
Ile Ser Ile Leu Phe Ile Asp Ser Ala Asn Asn Val Val Tyr Lys Gln
                475                             480                 485 tat gag gac atg gtc gtg gag tcg tgt ggc tgc agg tagcagcact              2017
Tyr Glu Asp Met Val Val Glu Ser Cys Gly Cys Arg
490                 495                 500 ggccctctgt cttcctgggt ggcacatccc aagagcccct tcctgcactc ctggaatcac       2077
agaggggtca ggaagctgtg caggagcat ctacacagct tgggtgaaag gggattccaa        2137
taagcttgct cgctctctga gtgtgacttg ggctaaaggc cccctttat ccacaagttc        2197 ccctggctga ggattgctgc ccgtctgctg atgtgaccag tggcaggcac aggtccaggg       2257
agacagactc tgaatgggac tgagtcccag gaaacagtgc tttccgatga gactcagccc      2317
accatttctc ctcacctggg ccttctcagc ctctggactc tcctaagcac ctctcaggag      2377
agccacaggt gccactgcct cctcaaatca catttgtgcc tggtgacttc ctgtccctgg      2437
gacagttgag aagctgactg ggcaagagtg ggagagaaga ggagagggct tggatagagt      2497
tgaggagtgt gaggctgtta gactgttaga tttaaatgta tattgatgag ataaaaagca      2557
aaactgtgcc taaaaaaaaa aaaaaaaaa aaaaaaaaaa aaaaaaaaa aaaaaaaaaa        2617 aaaaaaaaaa aaaaaaaaaa aaaaaa                                            2643
```

<210> SEQ ID NO 2
<211> LENGTH: 501
<212> TYPE: PRT
<213> ORGANISM: Homo sapiens
<220> FEATURE:
<221> NAME/KEY: misc_feature
<222> LOCATION: (1)..(501)
<223> OTHER INFORMATION: gene is "GDF5"

<400> SEQUENCE: 2

```
Met Arg Leu Pro Lys Leu Leu Thr Phe Leu Leu Trp Tyr Leu Ala Trp
1               5                   10                  15

Leu Asp Leu Glu Phe Ile Cys Thr Val Leu Gly Ala Pro Asp Leu Gly
                20                  25                  30

Gln Arg Pro Gln Gly Thr Arg Pro Gly Leu Ala Lys Ala Glu Ala Lys
            35                  40                  45

Glu Arg Pro Pro Leu Ala Arg Asn Val Phe Arg Pro Gly Gly His Ser
        50                  55                  60

Tyr Gly Gly Gly Ala Thr Asn Ala Asn Ala Arg Ala Lys Gly Gly Thr
65                  70                  75                  80

Gly Gln Thr Gly Gly Leu Thr Gln Pro Lys Lys Asp Glu Pro Lys Lys
                85                  90                  95

Leu Pro Pro Arg Pro Gly Gly Pro Glu Pro Lys Pro Gly His Pro Pro
            100                 105                 110

Gln Thr Arg Gln Ala Thr Ala Arg Thr Val Thr Pro Lys Gly Gln Leu
        115                 120                 125
```

```
Pro Gly Gly Lys Ala Pro Pro Lys Ala Gly Ser Val Pro Ser Ser Phe
    130                 135                 140

Leu Leu Lys Lys Ala Arg Glu Pro Gly Pro Arg Glu Pro Lys Glu
145                 150                 155                 160

Pro Phe Arg Pro Pro Ile Thr Pro His Glu Tyr Met Leu Ser Leu
                165                 170                 175

Tyr Arg Thr Leu Ser Asp Ala Asp Arg Lys Gly Asn Ser Ser Val
            180                 185                 190

Lys Leu Glu Ala Gly Leu Ala Asn Thr Ile Thr Ser Phe Ile Asp Lys
            195                 200                 205

Gly Gln Asp Asp Arg Gly Pro Val Val Arg Lys Gln Arg Tyr Val Phe
    210                 215                 220

Asp Ile Ser Ala Leu Glu Lys Asp Gly Leu Leu Gly Ala Glu Leu Arg
225                 230                 235                 240

Ile Leu Arg Lys Lys Pro Ser Asp Thr Ala Lys Pro Ala Ala Pro Gly
                245                 250                 255

Gly Gly Arg Ala Ala Gln Leu Lys Leu Ser Ser Cys Pro Ser Gly Arg
            260                 265                 270

Gln Pro Ala Ser Leu Leu Asp Val Arg Ser Val Pro Gly Leu Asp Gly
    275                 280                 285

Ser Gly Trp Glu Val Phe Asp Ile Trp Lys Leu Phe Arg Asn Phe Lys
290                 295                 300

Asn Ser Ala Gln Leu Cys Leu Glu Leu Glu Ala Trp Glu Arg Gly Arg
305                 310                 315                 320

Ala Val Asp Leu Arg Gly Leu Gly Phe Asp Arg Ala Ala Arg Gln Val
                325                 330                 335

His Glu Lys Ala Leu Phe Leu Val Phe Gly Arg Thr Lys Lys Arg Asp
            340                 345                 350

Leu Phe Phe Asn Glu Ile Lys Ala Arg Ser Gly Gln Asp Asp Lys Thr
            355                 360                 365

Val Tyr Glu Tyr Leu Phe Ser Gln Arg Arg Lys Arg Arg Ala Pro Leu
    370                 375                 380

Ala Thr Arg Gln Gly Lys Arg Pro Ser Lys Asn Leu Lys Ala Arg Cys
385                 390                 395                 400

Ser Arg Lys Ala Leu His Val Asn Phe Lys Asp Met Gly Trp Asp Asp
                405                 410                 415

Trp Ile Ile Ala Pro Leu Glu Tyr Glu Ala Phe His Cys Glu Gly Leu
            420                 425                 430

Cys Glu Phe Pro Leu Arg Ser His Leu Glu Pro Thr Asn His Ala Val
            435                 440                 445

Ile Gln Thr Leu Met Asn Ser Met Asp Pro Glu Ser Thr Pro Pro Thr
    450                 455                 460

Cys Cys Val Pro Thr Arg Leu Ser Pro Ile Ser Ile Leu Phe Ile Asp
465                 470                 475                 480

Ser Ala Asn Asn Val Val Tyr Lys Gln Tyr Glu Asp Met Val Val Glu
                485                 490                 495

Ser Cys Gly Cys Arg
            500
```

TARGETED DELIVERY OF THERAPEUTIC AGENTS WITH LYOPHILIZED MATRICES

CROSS-REFERENCE TO RELATED APPLICATIONS

This application claims the benefit under 35 U.S.C. §371 of International Patent Application No. PCT/US2007/83219, filed on Oct. 31, 2007, and titled "Targeted Delivery of Therapeutic Agents with Lyophilized Matrices," which claims the benefit under 35 U.S.C. §119(e) of U.S. Provisional Patent Application No. 60/855,774, filed on Oct. 31, 2006, and titled "Freeze-dried Tendon Allografts as Delivery for Genes," and U.S. Provisional Patent Application No. 60/855,941, filed Nov. 1, 2006, and titled, "Freeze-dried Tendon Allografts as Delivery for Genes"; the entirety of all these applications is hereby incorporated by reference.

GOVERNMENT LICENSE RIGHTS

This invention was made with government support under AR056696 awarded by National Institutes of Health. The government has certain rights in the invention.

SEQUENCE LISTING

The instant application contains a Sequence Listing which has been submitted via EFS-Web and is hereby incorporated by reference in its entirety. Said ASCII copy, created on Apr. 28, 2010, is named 769080077.txt and is 13,753 bytes in size.

FIELD OF THE INVENTION

Embodiments of the invention relate to systems and methods for gene therapy and drug delivery.

BACKGROUND OF THE INVENTION

Tendon, ligament, and joint capsular injuries represent 45% of the almost 33 million musculoskeletal injuries each year in the United States, and hand injuries account for 5-10% of annual emergency department visits nationwide (Praemer et al., 1999). Common among these injuries are flexor tendon lacerations, concomitant with injury to adjacent structures, as well as ruptures, especially in individuals active in sports (Leddy, 1988). Successful repair of ruptured flexor tendons, as measured by return of gliding function, is a great challenge to hand surgeons because of the nature of tendon repair, which often results in indiscriminate adherence of the tendon to surrounding tissue (Schneider & Hunter, 1988).

The surgeon's objective in repair is to create an environment in which the injured tendon can heal with a minimal amount of fibrosis and tissue reaction, and then following an initial protection period, to undergo controlled physical therapy regimens to mobilize the repaired tendon, and ensure restoration of the gliding function, while minimizing the risk of re-injury (Leddy, 1988; Schneider & Hunter, 1988).

SUMMARY OF THE INVENTION

The challenge in effecting successful soft tissue repair is largely due to the variability and unpredictability in the process of tendon repair, that almost invariably leads to significant adhesions resulting from as little insult as the passing of a suture through the tendon (Lindsay et al., 1960).

Accordingly, there is provided in some embodiments, a surgical graft, for use in promoting healing of a diseased or injured tissue, comprising: a nonviable, substantially acellular, lyophilized, biologically derived matrix; and at least one therapeutic agent, releasably coupled to the matrix; wherein the graft is sized and shaped to be placed in a patient's body in proximity to a diseased or injured tissue; wherein, when the graft is placed in the body, the at least one therapeutic agent is released into the tissue; and wherein the at least one therapeutic agent is effective to promote healing of the tissue.

In some embodiments, the healing comprises at least one of tissue remodeling, accelerating wound healing, achieving a reduced adhesion coefficient, and enhancing cell repopulation. In some embodiments, the healing comprises at least one of improving joint flexion, improving joint range of motion, and improving tendon gliding.

In some embodiments, the matrix comprises a collagen. In some embodiments, the collagen is derived from at least one of tendon and ligament.

In some embodiments, the at least one therapeutic agent is adsorbed to the matrix. In some embodiments, release of the at least one therapeutic agent is a sustained release.

In some embodiments, the at least one therapeutic agent comprises: an expression system, configured to result in expression of at least one therapeutic protein; wherein the expression system comprises at least one of a virus, a plasmid, a bacteriophage, a chromosome, a yeast artificial chromosome, a cosmid, and a linear DNA fragment.

In some embodiments, the therapeutic agent comprises a recombinant adeno-associated virus. In some embodiments, the expression system comprises a nucleic acid comprising at least about 80% sequence identity to (a) a nucleic acid from about position 500 to about position 2020 of SEQ ID NO: 1, or (b) the complement of the nucleotide sequence of (a).

In some embodiments, the expression system comprises a nucleic acid encoding a protein having at least about 80% sequence identity to a protein defined by SEQ ID NO: 2.

In some embodiments, the at least one therapeutic agent comprises a GDF5 receptor agonist. In some embodiments, the GDF5 receptor agonist comprises a protein having substantial homology to a protein as defined by SEQ ID NO: 2. In some embodiments, the GDF5 receptor agonist comprises an antibody configured to bind and activate a GDF5 receptor. In some embodiments, the at least one therapeutic agent comprises a protein having at least about 80% sequence identity to a protein as defined by SEQ ID NO: 2.

In some embodiments there is provided a method, of promoting healing of a diseased or injured tissue, comprising: providing a graft, comprising: a nonviable, substantially acellular, lyophilized, biologically derived matrix; and at least one therapeutic agent, releasably coupled to the matrix; wherein the graft is sized and shaped to be placed in a patient's body in proximity to a diseased or injured tissue; wherein the at least one therapeutic agent is effective to promote healing of the tissue; and placing the graft in the body, such that the at least one therapeutic agent is released into the tissue.

In some embodiments of the method, the healing comprises at least one of tissue remodeling, accelerating wound healing, achieving a reduced adhesion coefficient, and enhancing cell repopulation. In some embodiments of the method, the healing comprises at least one of improving joint flexion, improving joint range of motion, and improving tendon gliding.

In some embodiments of the method, the matrix comprises a collagen.

In some embodiments of the method, the at least one therapeutic agent comprises: an expression system, configured to result in expression of at least one therapeutic protein;

wherein the expression system comprises at least one of a virus, a plasmid, a bacteriophage, a chromosome, a yeast artificial chromosome, a cosmid, and a linear DNA fragment. In some embodiments of the method, the therapeutic agent comprises a recombinant adeno-associated virus.

In some embodiments of the method, the expression system comprises a nucleic acid comprising at least about 80% sequence identity to (a) a nucleic acid from about position 500 to about position 2020 of SEQ ID NO: 1, or (b) the complement of the nucleotide sequence of (a).

In some embodiments of the method, the at least one therapeutic agent comprises a GDF5 receptor agonist.

In some embodiments of the method, the at least one therapeutic agent comprises a protein having at least about 80% sequence identity to a protein as defined by SEQ ID NO: 2.

In some embodiments of the method, the diseased or injured tissue comprises at least one of a rotator cuff, an Achilles tendon, a flexor tendon, an extensor tendon, a ligament, a bone, and cartilage.

SEQ ID NO: 1 is a cDNA sequence from *Homo sapiens* encoding GDF5.

SEQ ID NO: 2 is a deduced amino acid sequence of *Homo sapiens* GDF5.

DETAILED DESCRIPTION OF THE INVENTION

All references cited herein are hereby incorporated by reference in their entirety for all purposes.

Clinical and experimental observations suggest that formation of adhesions can be precipitated by injury to the tendon sheath, surgical manipulation, suturing of the tendon, and immobilization (Gelberman & Manske, 1985). Thus, while the initial treatment and primary surgical repair are important and often successful, complications related to post-operative restrictive adhesions (Lister, 1985) and subsequent rupture (Masada et al., 2002), are not uncommon, and can require surgical release of adhesions, or tenolysis. This is most challenging to tendon injury in the "no-man's land" or Zone II, which in the past were not repaired due to their poor prognosis (Leddy, 1988).

Surgeons are now increasingly using free and pedicled autograft and allograft tendons in single- or two-staged flexor system reconstruction and especially as a late management option for neglected flexor tendon injury (Schneider, 1985; Wehbe et al., 1986; Stark et al., 1989; Vermeylen & Monballiu, 1991; Tang et al., 1993; Tolat & Stanley, 1993; Morrison & Cleland, 1995; Sakellarides & Papadopoulos, 1996; Liu & Yang, 1997; Naam, 1997; Leversedge et al., 2000; Valenti & Gilbert, 2000; Coyle et al., 2002; Beris et al., 2003; Smith et al., 2004).

Flexor Tendon Grafts for Zone II Injuries

Figure 1:
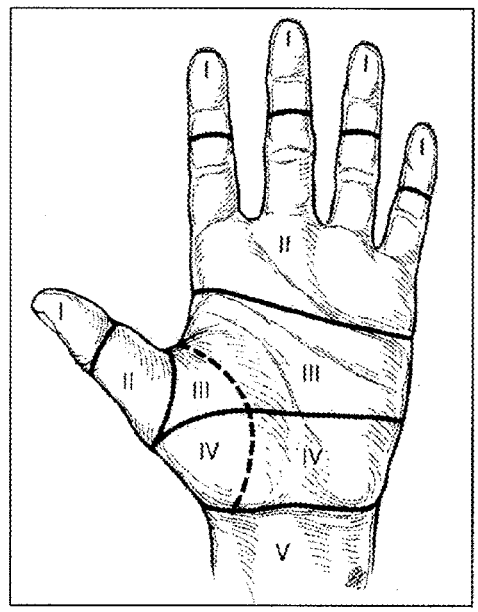
FIG. 1 illustrates the Flexor System Anatomical Zones (A); Zone II which lies within a fibro-osseous sheath can be repaired by a bridging tendon graft whose junctures can be attached distally and proximally in zones I and III, outside the confines of the sheath (B); an example of the flexor digitorum longus (FDL) grafting procedure (C); and a schematic illustrating the interposition of a live allograft or a lyophilized tendon allograft, implanted in the distal FDL tendon (D).
Figure 1:
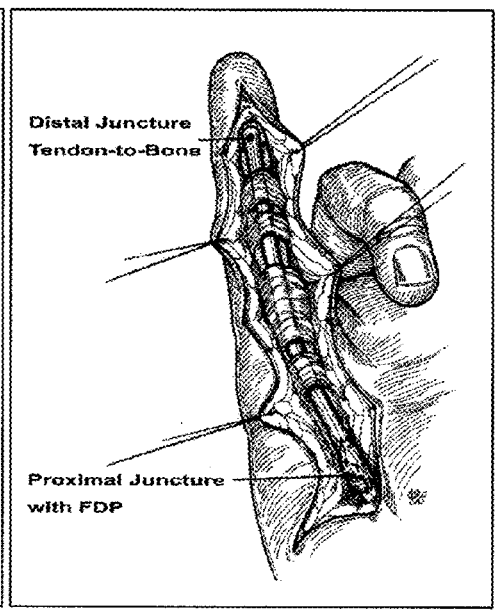
Figure 1:
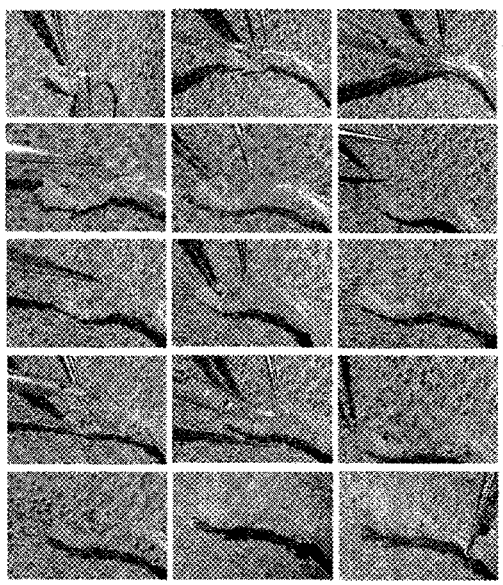
Figure 1:
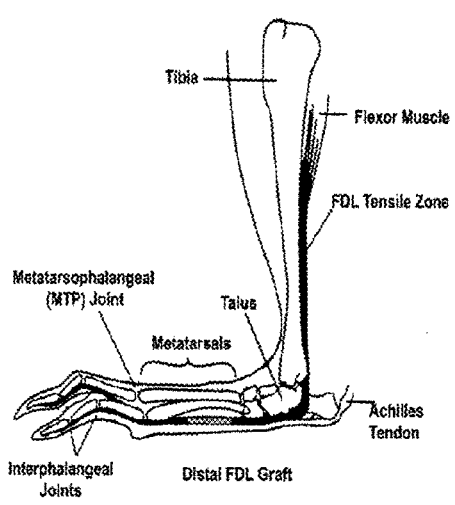

The flexor system is clinically divided into 5 anatomical zones, as shown in FIG. 1, of which Zone II which lies within a fibro-osseous sheath that when injured has a poor prognosis. Historically, this zone was known as "Bunnell's no man's land" because he once advised that primary repair in this area should be avoided (Bunnell, 1953). Anatomically, this zone lies within the flexor retinaculum from the mid-portion of the middle phalanx to the neck of the metacarpal (Schneider & Hunter, 1988). In this zone, the flexor digitorum profundus (FDP) passes through the tail of the flexor digitorum superficialis (FDS), and the two tendons glide within a tough fibrous sheath or retinaculum.

Injuries in this zone can sever either one or both of the flexor tendons. Unfortunately, such injuries generally have poor prognosis for restoration of gliding function (Schneider & Hunter, 1988), due to the development of extensive adhesion areas following injury and during primary repair. As an alternative to primary repair, the transplantation of a tendon graft allows the surgeon to place the graft junctures outside of the confines of the flexor sheath in zone II. The graft is thus attached distally in Zone I, where no gliding motion takes place, and in Zone III, proximal to the FDP tendon.

Other indications for flexor tendon grafting include cases where flexor tendon repair has been delayed. Delay can occur due to infection or other reasons, for example, where tendons have ruptured, and the severed ends are nonviable and cannot be effectively sutured together, or when a primary repair has failed. In these cases, continuity and gliding function of the FDP or FDS can often be restored by using a free, or pedicled, graft to bridge the defect (Stark et al., 1989).

Despite their elegance, flexor tendon grafting procedures are not without pitfalls, and can be very challenging even for the most experienced hand surgeon. The most persistent problem with tendon grafting is that adhesions will form whenever the surface of the live tendon graft has been violated either through suturing or from surgical manipulation (intrinsic fibrosis), or whenever the tendon sheath is disrupted (extrinsic fibrosis). The extent to which adhesions arise from intrinsic or extrinsic factors remains unclear. Regardless, in the event of adhesion complications, the more technically demanding surgical release of these adhesions (tenolysis) can be required, and if unsuccessful can worsen hand function (Taras & Kaufmann, 2005).

Animal Models of Flexor Tendon Grafts

Animal studies suggest that autogenous tendon grafts stimulate an intrinsic repair and remodeling process in both the tendon stumps and the autogenous graft itself (Singer et al., 1989; Gelberman et al., 1992; Ark et al., 1994; Abrahamsson et al., 1995; Seiler et al., 1997; Wu et al., 2000; Slade et al., 2001). For example, it was observed in a chicken toe model, that early repair of the FDP tendon-graft was mediated by proliferation and ingrowth of the epitenon cells, intermingled with newly-formed collagen fibers, suggesting that the tendon graft played a role in the repair (Wu et al., 2000). The study further demonstrated the importance of early passive mobilization and suggested that without mobilization adhesions obliterated the surface and occupied the space between the tendon graft and surrounding tissue (Wu et al., 2000).

Others have demonstrated the advantages of using vascularized autografts over free autografts in the restoration of gliding function of non-human primate flexor tendons (Singer et al., 1989). It has also been shown that the source of the donor autograft (intrasynovial vs. extrasynovial) is a determinant of the rate of repair and remodeling (Ark et al., 1994). In these studies intrasynovial tendon grafts implanted within the synovial sheaths of canine forepaws were populated predominantly by viable endogenous cells throughout the repair process with minimal cell necrosis and extrinsic fibroblast ingrowth, while extrasynovial tendons appear to act as scaffolds, undergoing extensive cellular death followed by ingrowth of new vessels and cells, leading to an extensive repair response (Ark et al., 1994; Seiler et al., 1997). This early cellular necrosis in extrasynovial grafts was consistently followed by the ingrowth of fibrovascular adhesions from the periphery. The formation of dense peripheral adhesions, obliterating the gliding surface of the tendon, led to diminished tendon excursion and proximal interphalangeal joint rotation (Seiler et al., 1997).

Other studies compared the healing of flexor tendon autografts and freeze-dried allografts implanted in the paws of dogs (Webster & Werner, 1983b). The implanted allografts appeared to be tolerated well by the host and to allow flexor tendon function similar to that allowed by autografts (Webster & Werner, 1983b). Mechanically, the tendon allografts and autografts were similar, but remained significantly weaker than normal tendons. It has been further demonstrated that extrinsic cells from the synovial capsule of the joint populated and contribute to the healing of lacerations within freeze-dried allografts implanted in canine and rabbit knee joints (Potenza & Herte, 1982; Chow et al., 1983). Others have reported that acellular allografts induce minimal adhesion formation in bovine flexor tendons (Ramesh et al., 2003a; Ramesh et al., 2003b).

Intrinsic and Extrinsic Factors in Flexor Tendon Graft Healing and Adhesion

The biological mechanisms of flexor tendon graft repair and adhesion formation are still poorly understood, despite being studied for decades in various animal models. Some believe that flexor tendons have an intrinsic capability for healing (Lundborg, 1976; Lundborg & Rank, 1978). Others believe that healing is extrinsically mediated by the fibroblastic and mesenchymal cells of the tendon paratenon and surrounding synovial sheath (Potenza & Herte, 1982; Chow et al., 1983). This latter observation is interesting since the reactive proliferation and inflammatory responses of these synovial sheath cells is greater than that of the endotenon cells and is thought to play important roles in the induction of adhesion formation (Khan et al., 1996; Khan et al., 2000). Whether or not adhesions are necessary for the repair process remains debatable.

The role of intrinsic and extrinsic factors in tendon repair has been investigated (Lundborg et al., 1980; Lundborg et al., 1985). Some studies indicate that intrinsic flexor tendon cells play important roles in the healing process (Lundborg & Rank, 1980; Lundborg et al., 1985), while others suggest that flexor tendon cells might secrete mitogenic or growth-promoting factors that contribute to the early stages of healing (Duffy et al., 1992). Still others have criticized these results (Potenza & Herte, 1982).

Acellular freeze-dried canine profundus tendon allografts implanted into knee joints of dogs remain intact and free of adhesions (Potenza & Herte, 1982). Furthermore, these allografts were covered by a layer of proliferating fibroblast-like cells that "healed" cuts that had been pre-made in the allografts, and re-cellularized and remodeled the allografts ends. Likely, the cells that populated and contributed to the healing of these cuts within the allografts originated from the synovial capsule of the joint, suggesting an extrinsic repair mechanism in intrasynovial environments (Potenza & Herte, 1982).

Later studies showed that rabbit flexor tendons with transverse lacerations do in fact possess an intrinsic repair capacity when cultured in vitro in the absence of extrinsic cell sources and without the benefit of nutrition from a circulating blood supply or the influence of synovial fluid (Manske et al., 1984). This repair apparently originates from epitenon fibroblasts that proliferate and migrate into the laceration site, forming collagen fibers that bridge the defect (Manske et al., 1985b).

Altogether, the literature suggests that flexor tendon repair can be accomplished both by extrinsic peripheral fibroblasts, as well as by intrinsic fibroblasts from the tendon itself. The mechanism of adhesion formation, however, is unclear. It has been suggested that the presence of inflammatory cells, in the synovial sheath and epitenon, during tendon healing induces synovial fibroblasts and epitenon cells to increase their production of fibronectin, which in turns provides a scaffold for subsequent adhesion formation (Wojciak & Crossan, 1993). While recent studies indicate that peripheral adhesions associated with flexor tendon healing are not essential to the repair process (Manske et al., 1985a), it remains unclear whether the source of these cell-mediated adhesions is intrinsic or extrinsic to the graft, and what molecular factors are involved in these adhesions.

Targeted Gene Delivery

A growing number of growth factors and cytokines have the potential to enhance native repair responses in tendons and ligaments. However, methods for topical application of these proteins to sites of injury for extended periods are lacking. A molecular approach in which genetically modified cells synthesize and deliver the desired growth factor in a time-regulated manner can be a powerful means, to overcome the limitations associated with the (topical) application or bolus delivery of growth factor proteins (Eming et al., 2004). However, these cellular approaches are not clinically or commercially feasible at this time. In some cases, local transfer of genes that encode the relevant healing factors may provide a solution to this problem (Gerich et al., 1997b).

The efficacy of different viral vector systems (including retrovirus and adenovirus) in mediating targeted and transient gene transfer has been demonstrated in vitro and in vivo (Gerich et al., 1996; Gerich et al., 1997a). In a recent study, recombinant adenovirus vectors expressing green fluorescent protein (AdGFP) or BMP-13 (AdBMP-13) demonstrated efficient dose-dependent transgene expression 12 days after in vivo injection in rabbit flexor tendons, even though the highest dose injected seemed to illicit some local inflammatory response (Mehta et al., 2005). Although adenovirus-induced inflammation can potentially be minimized by using lower viral titers, its impact on adhesion formation in the long term remains unknown.

Recently, methods were developed to utilize recombinant adeno-associated viruses (rAAV) for targeted gene delivery in bone allograft repair and integration (Ito et al., 2005; Koefoed et al., 2005). An advantage provided by rAAV over other viral systems lies in its limited immunogenicity, and lack of pathogenic viral genes (Chen et al., 2003). Furthermore, the rAAV vector is the only FDA approved viral system for human gene therapy, with promising properties including its ability to mediate efficient transient gene expression in a broad range of host tissues, including both dividing cells and non dividing cells (Chen et al., 2003).

Figure 2:
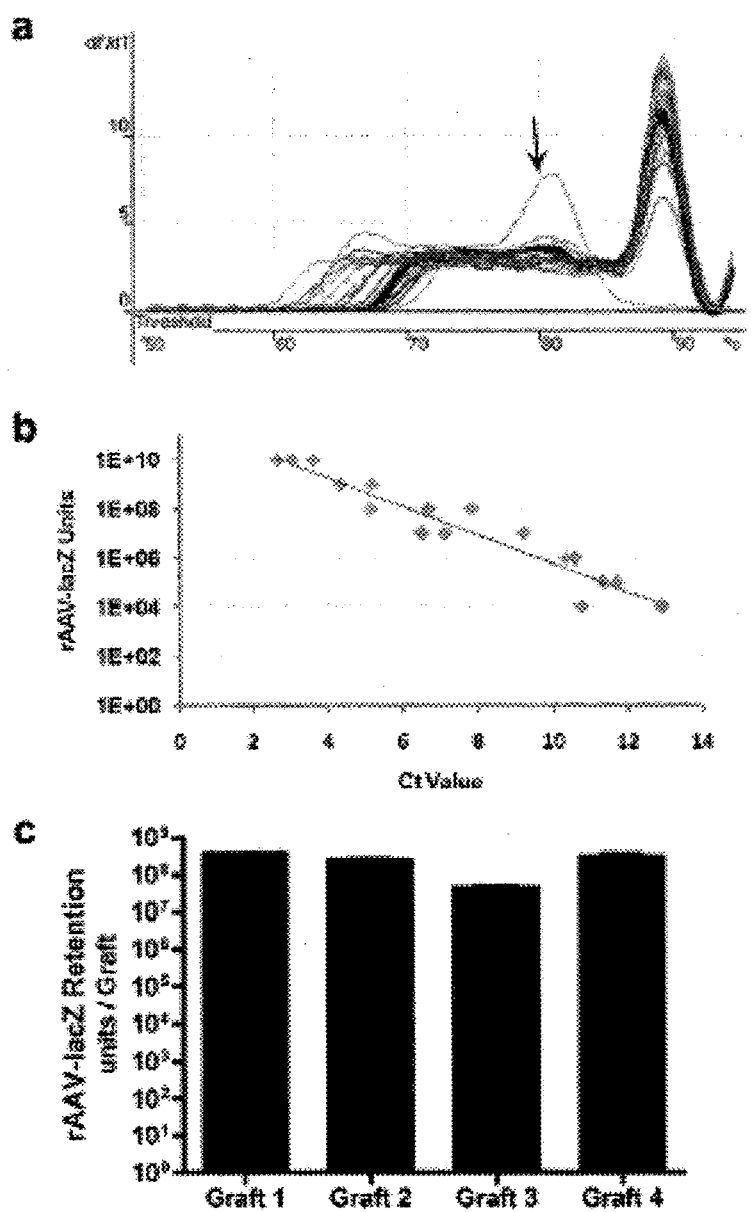
FIG. 2 illustrates retention efficiency of rAAV on lyophilized mouse FDL tendon allografts as assayed by real-time PCR: (A) Purity of PCR products as confirmed by melting curve analysis; (B) cycle threshold value versus number of rAAV particles; and (C) rAAV-LacZ retention in processed FDL tendon allografts.

In the present disclosure it has been determined that rAAV can be effectively retained in a viable form on a freeze-dried matrix. In some embodiments, retention efficiency of rAAV-LacZ was determined using freeze-dried FDL tendon grafts that had been reconstituted in a buffer containing $5\times10^9$ units of the vector. Quantitative real-time PCR was performed for rAAV-LacZ using LacZ specific primers. The purity of the PCR products was confirmed by the presence of a single peak in a melting point analysis. The peak shown by the arrow in FIG. 2A represents non-template controls. The cycle threshold (point at which reporter signal passes a defined level) was determined to be related to vector dosage, as shown in FIG.

2B. In four separate graft samples, retention of rAAV vector on the graft was estimated at 10.4±5.8%, as shown in FIG. 2C.

Embodiments of the present disclosure provide an advantage in that therapeutically effective agents are provided in a sustained fashion, for example, via ectopic expression of the agent in at least one cell type involved in healing and/or tissue remodeling.

GDF5 Role in Tendon Biology and Repair

Various growth factors such as transforming growth factor, epidermal growth factor, platelet-derived growth factor, and insulin-like growth factor can increase tendon cell proliferation and matrix formation in vitro and in vivo (Banes et al., 1995; Abrahamsson & Lohmander, 1996; Kashiwagi et al., 2004). Although for the most part all of these growth factors have a positive effect on collagen synthesis, cell proliferation, and in some cases tendon strength, they all have varied and complex effects throughout the body that are not limited to tendon and ligament biology (Hsu & Chang, 2004).

The murine growth and differentiation factors (GDFs) 5, 6, and 7 (also called BMP-14, -13, and -12) have recently been shown to be involved in tendon development and healing. All three growth factors can induce the production of tendon like tissue in vitro and in vivo (Wolfman et al., 1997; Morotome et al., 1998; Aspenberg & Forslund, 1999; Clark et al., 2001; Mikic et al., 2001; Rickert et al., 2001; Chhabra et al., 2003; Nakamura et al., 2003; Sena et al., 2003; Mikic, 2004).

Studies investigating GDF5 deficient mice have shown that this subfamily of proteins is essential for normal tendon development. For example, GDF5 deficiency in mice led to disruption of tail tendon form and function (Clark et al., 2001). This deficiency has also been shown to alter the ultrastructure, mechanical properties, and composition of the Achilles tendon and significantly delayed its healing in an injury model (Mikic et al., 2001; Chhabra et al., 2003; Mikic, 2004). An example of a GDF5 protein is provided by SEQ ID NO: 2.

Recent studies reported that adenovirus mediated GDF7 (BMP-12) gene transfer into chicken tendon cells in vitro increased type I collagen synthesis without changes in alkaline phosphatase activity. In vivo, GDF7 gene transfer in a complete tendon laceration chicken model resulted in a twofold increase in tensile strength, and stiffness, of repaired tendons (Lou et al., 2001). In a recent study, recombinant adenovirus vectors expressing green fluorescent protein (AdGFP) or BMP-13 (or GDF6; AdBMP-13) demonstrated efficient dose-dependent transgene expression 12 days after in vivo injection in rabbit flexor tendons (Mehta et al., 2005). Although adenovirus-induced inflammation can potentially be minimized by using lower viral titers, the impact on adhesion formation in the long term remains unknown. Others have shown that adenovirus-mediated GDF5 gene expression in rat Achilles tendons peaked after 2 weeks and persisted up to 4 weeks (Rickert et al., 2005).

Embodiments of the present disclosure provide compositions and methods for the delivery of therapeutic agents to a target tissue via acellular matrices. It has been discovered that, surprisingly, freeze-dried and acellular matrices can provide a satisfactory alternative to fresh tendon matrices. It has been further determined that nonviable matrices are useful in preventing or lessening adhesion formation, since manipulation of the matrices will not induce the insults that precede fibrosis and adhesion formation in live autografts. Additionally, nonviable matrices act as scaffolds to guide tissue repair and remodeling, while lacking the endogenous cells and intrinsic repair capabilities of live autografts—intrinsic capabilities that often result in a repair tissue with inferior tensile strength and increased likelihood of re-injury.

It has also been determined that providing an acellular matrices with a subset of intrinsic repair and remodeling factors (mitogenic, chemotactic, and angiogenic) prior to transplantation in vivo, can improve the repair strength while minimizing adhesions associated with cellular insult resulting from manipulating live grafts. These methods lead to significant advances in flexor tendon repair and hand surgery, for example.

In some embodiments, a method to modulate flexor tendon healing and successful elimination or reduction of fibrotic adhesion, involves loading a freeze-dried flexor digitorum longus (FDL) allograft with recombinant adeno-associated viral (rAAV) vectors for the targeted and transient expression of growth/differentiation Factor 5 (GDF5). Such methods can advance clinical management of one of the most challenging problems facing hand surgeons; namely adhesion-free flexor tendon grafting. In some embodiments, GDF5 protein can be directly provided to a healing tissue by loading onto a tissue allograft a pharmaceutical composition comprising pure or substantially pure GDF5.

DEFINITIONS

As used herein, the term "patient" refers to any human, or non-human animal, in which limiting formation of scar tissue adhesions following an injury to a tissue is indicated. Non-human animals can include mammals and non-mammals.

The term "polynucleotide" or "oligonucleotide" as used herein refers to a polymeric form of nucleotides of any length, either ribonucleotides, deoxyribonucleotides, or modified derivatives thereof. This term refers only to the primary structure of the molecule. Thus, this term includes double and single stranded DNA, triplex DNA, as well as double and single stranded RNA, including for example, and without limitation, siRNA, mRNA, and further includes hybrids of RNA and DNA. It also includes modified forms of the polynucleotide, for example and without being limiting, by methylation and/or by capping, as well as unmodified forms of polynucleotides.

The term "promoter region" refers to a DNA sequence that controls transcription of one or more nucleic acid sequences, located upstream with respect to the direction of transcription of the transcription initiation site of the gene, and which can be structurally identified by the presence of a binding site for DNA-dependent RNA polymerase, transcription initiation sites and any other DNA sequences, including, but not limited to transcription factor binding sites, repressor and activator protein binding sites, calcium or cAMP responsive sites, and any other nucleotide sequences known to act directly or indirectly to regulate transcription from the promoter.

The term "recombinant" as used herein refers to a polynucleotide of genomic, cDNA, semi-synthetic, or synthetic origin that by virtue of its origin or manipulation: (1) is not associated with all or a portion of the polynucleotide with which it is associated in nature and/or (2) is linked to a polynucleotide other than that to which it is linked in nature.

The term "cDNA" or "complementary DNA" refers to single stranded or double stranded DNA sequences obtained by reverse transcription of messenger RNA isolated from a donor cell. For example, treatment of messenger RNA with a reverse transcriptase such as AMV reverse transcriptase or M-MuLV reverse transcriptase in the presence of an oligonucleotide primer will furnish an RNA-DNA duplex which can be treated with RNase H, DNA polymerase and DNA ligase to generate double stranded cDNA. If desired, the double stranded cDNA can be denatured by conventional techniques such as shearing to generate single stranded cDNA.

The term "operably linked" refers to the linkage of a DNA segment to another DNA segment in such a way as to allow the segments to function in an intended manner. A DNA sequence encoding a gene product is operably linked to a regulatory sequence when it is ligated to the regulatory sequence, such as, for example and without limitation, promoters, enhancers and/or silencers, in a manner which allows modulation of transcription of the DNA sequence, directly or indirectly. For example, a DNA sequence is operably linked to a promoter when it is ligated to the promoter downstream with respect to the transcription initiation site of the promoter, in the correct reading frame with respect to the transcription initiation site, and allows transcription elongation to proceed through the DNA sequence.

An enhancer or silencer is operably linked to a DNA sequence coding for a gene product when it is ligated to the DNA sequence in such a manner as to increase, or decrease, the transcription of the DNA sequence. Enhancers and silencers may be located upstream, downstream or embedded within the coding regions of the DNA sequence. A DNA for a signal sequence is operably linked to DNA coding for a polypeptide if the signal sequence is expressed as a pre-protein that participates in the secretion of the polypeptide.

Linkage of DNA sequences to regulatory sequences is typically accomplished by ligation at suitable restriction sites or via adapters or linkers inserted in the sequence enzymes and chemical methods known to one of skill in the art.

The terms "freeze-dried," "freeze-drying," and "freeze-dryer" are to be given their ordinary meaning, and are interchangeable with the terms "lyophilized," and "lyophilizing," and "lyophilizer."

The term "therapeutic composition" as used herein refers to a formulation that can be associated with the acellular matrices of the present disclosure. The therapeutic composition can be associated with an acellular matrix prior to, or after, freeze drying. A freeze dried acellular matrix can be reconstituted in a therapeutic composition solution. A therapeutic composition comprises at least one therapeutic agent.

The term "therapeutic agent" as used herein refers to any moiety or substance that confers a therapeutic response on a target tissue. Exemplary classes of therapeutic agents include but are not limited to small molecules, proteins, e.g., antibodies, nucleic acids, e.g., RNA, DNA, siRNA, ribozymes, and viruses, or any biologically effective fragment or portion thereof.

Therapeutic agents include Growth and Differentiation Factor 5, 6 and 7 (GDF5, -6 and -7) receptor agonists. In some embodiments the agents are the GDF5, -6 and -7 proteins themselves. These proteins and the nucleic acids that encode them, are described in detail in U.S. Pat. No. 5,801,014, U.S. Pat. No. 5,986,058, and U.S. Pat. No. 6,090,563, respectively, the entire contents of all of which are hereby incorporated by reference. In some embodiments, a GDF receptor agonist, comprises an antibody, or a portion thereof, configured to specifically bind and activate a GDF receptor. In some embodiments, the GDF receptor comprises a GDF5 receptor.

Growth and Differentiation Factor 5 (GDF5; Accession number gi:5123452) protein is a member of the bone morphogenetic protein (BMP) family and the TGF-β superfamily. GDF5 has been shown to be a key regulator of cartilage formation and segmentation of digits (joint formation). This group of proteins is characterized by a polybasic proteolytic processing site which is cleaved to produce a mature protein containing seven conserved cysteine residues.

Abnormally low or high levels of GDF5 may be indicative of various bone dysplasias such as epiphyseal, physeal (growth plate), metaphyseal and diaphyseal hypo- and hyperplasias. Examples of such diseases which may be diagnosed and/or treated using GDF5 polynucleotides and antibodies include: spondyloepithyseal dysplasia, dysplasia epiphysialis hemimelica, achondroplasia, metaphyseal dysostosis, hyperchondroplasia, enchondromatosis, hypophosphatasia, osteopetrosis, craniometaphyseal dysplasia, osteogenesis imperfecta, idiopathic osteoporosis, Engelman's disease and hyperphosphatasia (See: Harrison's Principles of Internal Medicine, McGraw-Hill Book Co., N.Y., 1987, Chpt. 339). For an description of GDF5 protein and variants thereof see U.S. Pat. No. 6,090,563 and U.S. Pat. No. 5,801,014.

Signaling of the TGF-β superfamily members requires ligand binding to cell surface receptors, consisting of two transmembrane serine-threonine kinase receptors classified as type I and II. These receptors form homodimeric and heterodimeric complexes on the cell surface consisting of type I and II receptor monomers. Two BMP type I receptors (BMPR1A and BMPR1B) and one type II receptor (BMPR2) are presently known. Ligand binding results in transphosphorylation of the type I receptor by the type II receptor. Activated BMPR1s transduce signals to the nucleus to control the transcription of target genes, mainly by phosphorylating members of the Smad family of transcriptional activators. GDF5 mediates its signaling activity through the BMP type I receptor (BMPR1B) (Seemann et al., 2005).

GDF5 protein contains all of the highly conserved residues present in other family members, including seven cysteine residues with characteristic spacing. Among the known family members, GDF5 is most highly related to BMP-2 and BMP-4 in the C-terminal portion of the molecule (57% amino acid sequence identity calculated from the first conserved cysteine).

Minor modification of a recombinant GDF5 coding sequence can result, when translated in a modified protein that retains substantially equivalent activity as compared to the GDF5 polypeptide described herein. Such modifications may be deliberate, as by site-directed mutagenesis, or may be spontaneous, or naturally-occurring. All of the polypeptides produced by these modifications are included herein as long as some biological activity of GDF5 remains. Further, deletion of one or more amino acids can also result in a modification of the structure of the resultant molecule without significantly altering its biological activity. This can lead to the production of a smaller active molecule with other utilities. For example, one can remove amino or carboxy terminal amino acids which are not required for GDF5 biological activity.

As an example of a method for determining biological activity of GDF5 in vivo, U.S. Pat. No. 5,801,014 discloses the construction of transgenic mice that ectopically express GDF5. The GDF5 coding sequence was cloned into the pMSXND expression vector (Lee & Nathans, 1988), and a fragment containing the metallothionein promoter/GDF5 cassette gel-purified and used to generate transgenic mice by standard methods known in the art. Analysis of two independent transgenic mouse lines showed that these animals displayed ectopic bone formation. A further example of how the biological activity of GDF5 expression can be measured is illustrated in Example 5.

Proteins that are substantially similar to GDF5 are encoded by nucleic acids that are substantially identical to SEQ ID NO: 1. The skilled artisan will also appreciate that oligonucleotide sequences substantially identical to SEQ ID NO: 1 may differ from SEQ ID NO: 1, respectively, with respect to the identity of at least one nucleotide base. However, all polynucleotides sequences substantially identical to SEQ ID NO: 1 will hybridize under stringent conditions (as defined herein) to all or a portion of the complements of SEQ ID NO: 1 (i.e., the target sequence), respectively. The terms "hybridize(s) specifically" or "specifically hybridize(s)" refer to complementary hybridization between an polynucleotides (e.g., a primer or labeled probe) and a target sequence. The term specifically embraces minor mismatches that can be accommodated by reducing the stringency of the hybridization media to achieve the desired priming for amplification by PCR, or for detection of hybridization signal, by blotting or other methods that screen for nucleic acid hybridization, including, but not limited to Southern blotting, Northern blotting, and FRET analysis.

Under stringent hybridization conditions generally only highly complementary (i.e., substantially identical nucleic acid sequences) will hybridize. In some cases, such conditions prevent hybridization of nucleic acids having 3 or more mismatches out of 20 contiguous nucleotides, in some cases 2 or more mismatches out of 20 contiguous nucleotides, and in some cases one or more mismatch out of 20 contiguous nucleotides. The hybridizing portion of the hybridizing nucleic acid is at least about 90%, but can be about 95%, or about 98%, identical to the sequence of a target sequence, or its complement. Hybridization of a nucleic acid to a nucleic acid sample under stringent conditions is defined below.

The relative stability of nucleic acid complexes is expressed as a melting temperature ($T_m$), which is the midpoint of the temperature range over which strands of nucleic acids separate, for example, a single-stranded DNA probe separating from a complementary target DNA. This melting temperature can be used to define relative conditions of stringency for hybridization. If sequences are to be identified that are substantially identical to the probe, rather than identical, then it is useful to first establish the lowest temperature at which only homologous hybridization occurs with a particular concentration of a salt and buffer combination (e.g., SSC or SSPE). Assuming that 1% mismatching results in a 1° C. decrease in $T_m$, the temperature of the final wash in the hybridization reaction can be reduced accordingly (for example, if sequences having >95% identity with the probe are sought, the final wash temperature is decrease by 5° C.). In practice, the change in $T_m$ can be range between about 0.5° C. and about 1.5° C. per 1% of mismatch between hybridizing nucleic acid strands.

For example, and without being limiting, stringent hybridization is performed at 68° C. in 5×SSC/5×Denhardt's solution/1.0% SDS, with washing in 0.2×SSC/0.1% SDS at room temperature. Moderately stringent conditions include washing in 3×SSC at 42° C. The parameters of salt concentration and temperature may be varied to achieve optimal level of identity between the primer and the target nucleic acid. Additional guidance regarding such conditions is readily available in the art (See: Sambrook et al., *Molecular Cloning, a laboratory manual*, (2nd ed.), Cold Spring Harbor Laboratory Press, New York, (1989); Ausubel et al. eds., *Current Protocols in Molecular Biology*, John Wiley and Sons (1994)).

Moreover, those of skill in the art will also understand that it is possible that nucleic acids that are not substantially identical to SEQ ID NO: 1 will nonetheless produce, when translated, a protein product substantially identical to SEQ ID NO: 2, due to the degenerate nature of the genetic code.

In some embodiments the therapeutic agents are Growth and Differentiation Factor 5 (GDF5) receptor agonists ("GDF5 receptor agonists"). GDF5 receptor agonists are molecules that emulate to a varying degree, the natural signaling function of GDF5 protein through its receptor. For example, such agonists can be the GDF5 protein itself or substantially similar variants and/or fragments thereof that nonetheless specifically bind and activate the GDF5 receptor. In some embodiments, effective agonists can be small molecules that specifically bind and activate the GDF5 receptor. In some embodiments, effective agonists can be antibodies, e.g., F(ab) fragments, single chain Fv ("sFv") polypeptides or complete antibodies, that specifically bind and activate the GDF5 receptor. The term GDF5 receptor agonist as used herein also encompasses nucleic acids that encode proteins able to specifically bind and activate GDF5 receptors. Such proteins may be the GDF5 protein itself or substantially similar variants and/or fragments thereof as well as antibodies that specifically bind and activate the GDF5 receptor; that specifically bind and activate the GDF5 receptor.

In some embodiments, the therapeutic agent can be provided in the form of an "expression system." An expression system can comprise any genetic element, or combination of genetic elements, for example, a plasmid, chromosome, virus, capable of bringing about the expression of a therapeutic proteins, for example, and without being limiting, a GDF5 receptor agonist. These are referred to herein as GDF5 expression systems, or GDF5 expression vectors. In some embodiments, the GDF5 expression vectors comprise a nucleic acid substantially similar or identical to SEQ ID NO: 1, which when translated is capable of resulting in production of a protein substantially similar or identical to SEQ ID NO: 2. In some embodiments as described herein, such proteins are effective to result in reduced formation of adhesions in a target tissue.

Suitable expression systems or vectors can include, but are not limited to, viruses, plasmids, bacteriophages, yeast artificial chromosomes (YACs), cosmids, and the like. Vectors may contain polynucleotide sequences which are necessary to effect ligation or insertion of the vector into a desired host cell and the expression of its therapeutic protein coding region(s). Various viral vectors which can be utilized for gene therapy as taught herein include adenovirus, herpes virus, vaccinia, or an RNA virus, for example a retrovirus. In some embodiments, vectors include multiple genetic elements and can transfer or incorporate a gene for a selectable marker or reporter nucleic acid such that transfected cells can be identified, isolated and further propagated. In some embodiments the expression vectors can be adeno-associated virus (AAV) vectors.

Some embodiments of the expression vectors described herein contain nucleic acid sequences to facilitate expression of therapeutic proteins in a target tissue. These sequences can include regulatory elements that increase expression from the system either in response to the presence of an expression inducer, or in the absence of an expression repressor. Such sequences can include promoter sequences, for example, but not limited to, a polyhedrin promoter, SV40 promoter, or a conditionally activated promoter, for example, an inducible metallothionein promoter, or a tetracycline responsive promoter, to effect transcription; enhancer sequences to increase transcription; ribosomal binding site sequences; and transcription and translation termination sequences. The vector can also optionally behave either as an autonomous unit of polynucleotide replication within a cell (i.e., capable of replication under its own control) or it can be rendered capable of replication, for example, by insertion into a host cell chromosome, having attached to it another polynucleotide segment, so as to bring about the replication.

Dependovirus adeno-associated virus belongs to the Parvoviridae. Adeno-associated virus (AAV) is so named as it is often found in cells that are simultaneously infected with adenovirus. The virus is a small (20 nm) replication-defective, non-enveloped virus of mammals (including humans), which has not been associated with any known diseases. Adeno-associated virus has been extensively researched as a vector for gene therapy as it possesses many advantages in this regard. Advantages for gene therapy include a relative lack of pathogenicity, the ability to infect non-dividing cells, and the ability to stably integrate into the host cell genome at a specific site (designated AAVS1; human chromosome 19).

The AAV genome integrates most frequently into the site mentioned, while random incorporations into the genome take place with a negligible frequency. Adeno-associated viruses also present very low immunogenicity, restricted only to generation of neutralizing antibodies, and they induce no cytotoxic response. This feature, along with the ability to infect quiescent cells present their dominance over adenoviruses as vectors for the human gene therapy (Grieger & Samulski, 2005).

The term "reporter nucleic acid sequence" refers to a DNA molecule that expresses a detectable gene product, which may be reporter RNA or reporter protein. The detection may be accomplished by any method known to one of skill in the art. For example, detection of mRNA expression may be accomplished by using, for example, Northern blot analysis, dot blot analysis, and detection of protein may be accomplished by staining with antibodies specific to the protein, for example, Western blot analysis or immuno dot blot analysis. Useful reporter nucleic acid sequences are those that are readily detectable. A reporter nucleic acid sequence can be operably linked in a DNA construct with a regulatory DNA sequence such that detection of the reporter nucleic acid sequence product provides a measure of the transcriptional activity of the regulatory sequence. Examples of reporter nucleic acid sequences include, but are not limited to, those coding for alkaline phosphatase, chloramphenicol acetyl transferase (CAT), luciferase, β-galactosidase and alkaline phosphatase.

The terms "infected," "transformed," or "transfected," are used interchangeably and refer to the process by which exogenous DNA or RNA, for example, from an expression vector or portions thereof, is transferred or introduced into an appropriate host cell. A transfection procedure will in general prepare a host cell to become competent to take up exogenously added nucleic acid. The procedure can also include packaging the polynucleotide in a virus as well as direct uptake of the polynucleotide. Transformation can result in incorporation of the inserted DNA into the genome of the host cell or the maintenance of the inserted DNA within the host cell in a self-replicating form such as a plasmid, cosmid, or yeast artificial chromosome (YAC).

Other therapeutic agents can include a wide range of anti-inflammatory agents such as corticosteroids or non-steroidal anti-inflammatory drugs (NSAIDs); or antibiotics for example.

"Acellular matrix," as used herein, refers to a material that is devoid of cellular material. The matrix can be comprised of organic, materials, inorganic materials, such as ceramics, or synthetic polymers. Examples of organic materials that can be used to form the matrix include, but are not limited to, collagen, polyamino acids, or gelatin. The collagen source can be allogenic, or xenogeneic relative to the mammal receiving the implants. The collagen can also be in the form atelopeptide or telopeptide collagen.

Example of synthetic polymers that can be used to form a matrix include, but are not limited to, polylactic acids, polyglycolic acids, or combinations of polylactic/polyglycolic acids. Resorbable polymers, as well as non-resorbable polymers, for example, can constitute the matrix material. One of skill in the art will appreciate that the terms porous or semi-porous refer to the varying density of pores in a matrix. One of skill in the art will also appreciate that inorganic fillers or particles, such as, and without being limiting, hydroxyapatite, tri-calcium phosphate, ceramic glasses such as Bioglass®, amorphous calcium phosphates, porous ceramic particles or powders, mesh or particulate titanium or titanium alloy can be added to the organic or synthetic matrix. Mineralized or partially mineralized freeze-dried, particulate bone can also be used for this purpose.

Suitable and exemplary matrices are described in U.S. Pat. No. 5,707,962, the entire contents of which are herein incorporated by reference. Matrices that are biocompatible and biodegradable, and which can be formed in vitro or in vivo, at the time of implantation, and which are capable of releasably incorporating, and retaining activity of, therapeutic agents, for example, growth factor proteins, are described in U.S. Pat. No. 6,894,022, the entire contents of which are herein incorporated by reference. In some embodiments, an acellular matrix can be freeze-dried tendon or ligament tissue, using methods known in the art.

In some embodiments, the acellular matrix can be freeze-dried prior to delivery to a clinician. The freeze-dried matrix can be reconstituted in a therapeutic composition solution prior to its implantation in a patient. Alternatively, the acellular matrix can be associated with the therapeutic agent and then freeze-dried. In some embodiments, the freeze-dried therapeutic composition associated matrix can be readily deployed by the clinician with minimal preparation.

The term "adhesions" as used herein relates to internal scars and/or strand-like fibrous tissue that can form an abnormal bond between two parts of the body after injury, through complex processes involving injured tissues. Adhesions can cause severe clinical consequences. Any injury can result in fibrous adhesion formation. Adhesions have been found in patients undergoing first time surgery. For example, and without limitation, infection, endometriosis, chemotherapy, radiation and cancer can damage tissue and initiate the formation of adhesions.

Most commonly, adhesions occur during the first three to five days after surgery, as part of the body's normal healing process. Surgical procedures most commonly associated with adhesion formation are, for example, ovarian cystectomy, myomectomy, total abdominal hysterectomy, salpingostomy/fimbrioplasty, excision of endometriosis, excision of eptopic pregnancy, cesarean section, and adhesiolysis. Following reproductive pelvic surgery performed by laparotomy, patients can be found to have adhesions at subsequent surgeries. Not surprisingly, the number of hospital readmissions for adhesion related complications rival the number of operations for heart bypass, hip replacements and appendix operations. Adhesions involving the female reproductive organs, the ovaries, fallopian tubes, etc., can cause dyspaareunia (painful intercourse) infertility, and debilitating pelvic pain.

The biological mechanisms involved in the pathogenesis of flexor tendon adhesion following auto- and allograft transplantation are still poorly understood, despite being studied for decades in various animal models. Unexpectedly, it has been found that freeze-dried allografts used in transplantation procedures, offer substantially the same biomechanical advantages as fresh autografts. Further, the present disclosure demonstrates the feasibility of associating such matrices with expression vectors useful as a gene delivery platform. Specifically, the inventors have discovered that transient and localized rAAV-mediated transfer of the GDF5 gene via freeze-dried FDL allografts can be effective to induce accelerated remodeling of the graft. This can lead to early elimination of adhesions and restoration of tendon gliding and a more robust biomechanical improvement. The rate and extent of healing and remodeling can be AAV titer-dependent. As such, embodiments of the compositions and methods disclosed herein are used to prevent the formation of adhesions. In some embodiments, compositions and methods can be used to prevent the formation of adhesions resulting from surgery, particularly hand surgery.

EXAMPLES

It is to be understood that the exemplary embodiments provided herein are not intended to be limiting, and they are capable of use in various other combinations and environments, and are also capable of changes or modifications, without departing from the scope of the inventive concept as expressed herein. Thus, for example, those skilled in the art will recognize, or be able to ascertain, using no more than routine effort, numerous equivalents to the specific substances and procedures described herein. Such equivalents are considered to be within the scope of this disclosure.

Embodiments as described provide allografts that can be efficiently loaded with biologically active molecules, for example, therapeutic agents, that are releasably coupled to a matrix. On introduction into a patient near a healing tissue, the grafts are effective to release the therapeutic agents into the healing tissue in order to promote the healing process, as well as to influence tissue remodeling. Unlike prior art biomaterial scaffolds, the matrices of the present disclosure release therapeutic agents over a sustained period of time, likely due to interstitial water bound within the negatively charged matrix, which aids in retaining therapeutic agents, and controls the rate of their release. In addition, biologically derived matrices, for example tendon or ligament, comprise molecules such as small leucine-rich proteoglycans that aid in sequestration of therapeutic and other factors.

An additional advantage of embodiments of the present disclosure us that the freeze-drying technique results in a stable allograft which an essentially indefinite shelf-life, but which retains the biochemical properties of the matrix such that the freeze-dried matrix performs at least as well as fresh material. Freeze-drying also avoids prior art methods of fixation, which can chemically alter a matrix, which can create concerns with respect biological safety or antigenicity.

Example 1

A Murine Distal FDL Tendon Graft Model to Study Repair and Adhesions

To investigate the cellular, molecular, and biomechanical aspects of scarring and adhesion formation following flexor tendon grafting, a mouse distal flexor digitorum longus (FDL) tendon grafting model was developed. Briefly, the FDL tendon was isolated and a 3 mm defect created in the distal FDL on the plantar surface of the metatarsal, as shown in FIGS. 1C and 1D. An interposition freeze-dried tendon allograft or live autograft was sutured between the ends of host tendon using 8-0 nylon sutures and reconstituted with sterile normal saline. The tendon was then transected at the proximal musculotendinous junction to temporarily immobilize the flexor mechanism, which in turn prevents disruption of the tendon graft early in the repair period, and to provide a stimulus for adhesion formation. Mice were sacrificed at multiple end point times, up to 84 days post surgery, to evaluate tendon adhesion non-destructively and quantitatively; and subsequently to test the repair strength and biomechanical stiffness in failure tensile tests.

Figure 3:
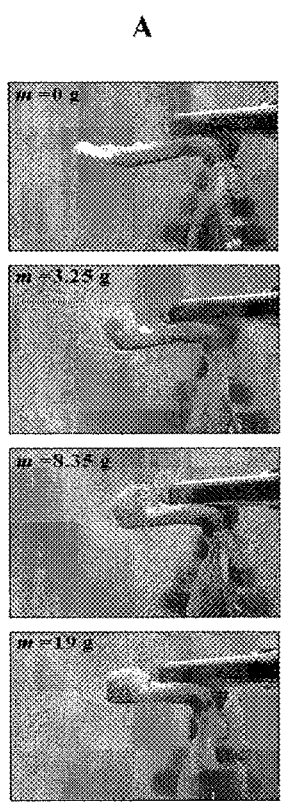
FIG. 3 illustrates an example of: (A) an adhesion testing experiment based on metatarsophalangeal (MTP) joint flexion; (B) representative flexion curves of the MTP joint in normal and grafted FDL tendons; (C) adhesion coefficient of live autograft (black bars) and freeze-dried allograft (white bars) FDL tendon repairs up to 84 days post transplantation (mean±standard error of the mean (SEM)); and (D) correlation between the empirically determined adhesion coefficient and the MTP flexion range of motion (ROM).
Figure 3:
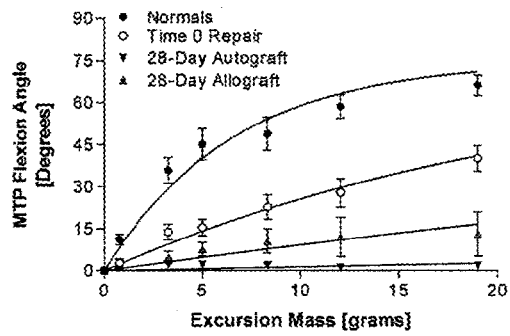
Figure 3:
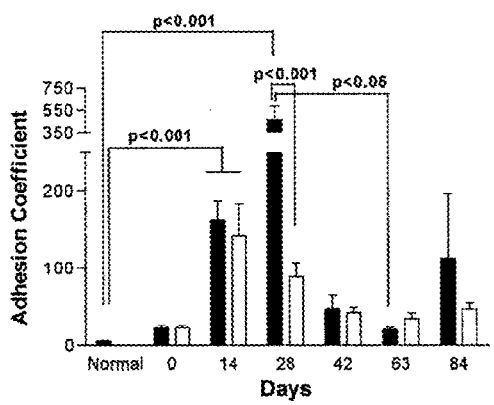
Figure 3:
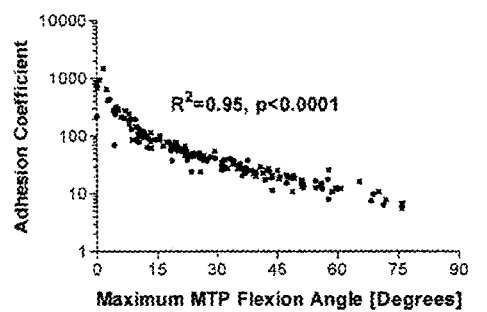

To evaluate the metatarsophalangeal (MTP) flexion range of motion (ROM), a novel assay to quantify the resistance to flexion due to adhesion formation in the grafted FDL tendon was developed. Briefly, the lower hind limb was disarticulated from the knee, and the proximal FDL tendon along the tibia is transected from the musculotendinous juncture and released just proximal the tarsal tunnel without disrupting the skin at the ankle or foot. The proximal end of the tendon was then sandwiched between two square pieces of tape using a cyanoacrylate adhesive. The lower hind limb was fixed in a custom holding apparatus where the tibia was rigidly held to prevent rotation, while the plantar face of the foot was rested against a flat surface, as shown in FIG. 3.

Figure 4:
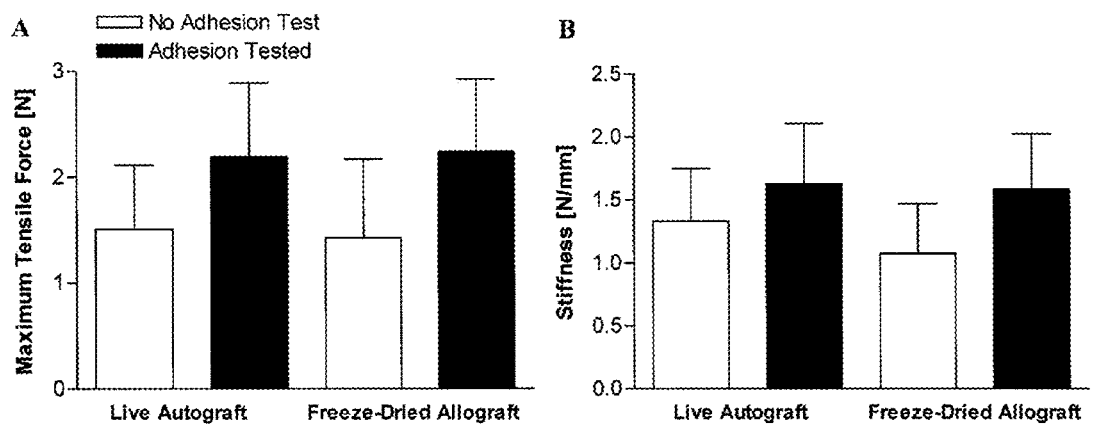
FIG. 4 illustrates effects of the non-destructive adhesion test on: (A) maximum tensile force; and (B) stiffness of live autografts and freeze-dried allografts.

A hook and a line were passed through the proximal FDL tendon and tape sandwich. The toes were extended and a digital image taken medially for the neutral position (zero load) of the MTP joint. The FDL tendon was incrementally loaded using dead weights (ranging from about 0 g to about 19 g) in the same anatomical direction as flexor muscle force would act. In the example, the maximum weight of 19 g was about 10% of the failure force of the grafts at 14 days, the earliest time point tested. Therefore, this test can be classified as non-destructive as it produced no adverse effects on the grafted tendon biomechanics, as shown in FIG. 4.

The toes were allowed to flex to an equilibrium position at every incremental load application and digital images were taken medially at each applied load to quantify the MTP flexion angle relative to the zero load neutral position. The digital images were subsequently loaded to a computer and the MTP joint flexion angle and range of motion (ROM) was measured with ImageJ software.

The MTP joint flexion angle was plotted versus the applied excursion loads, as shown in FIG. 3B. Based on the flexion curve of the normal tendon, the flexion data were modeled using a single-phase exponential association equation of the form:

$$\text{Flexion Angle} = \beta \times [1 - \exp(-m/\alpha)] (R^2 = 0.83, p < 0.05);$$

where m is the applied excursion load. The curve fit was physically constrained by a maximum flexion angle ($\alpha$) that was set at 75°. The constant ($\beta$) governing the rate of the rise of the flexion curve with increased loading is representative of the resistance to flexion which is due to adhesions and is therefore termed the adhesion coefficient. This novel adhesion coefficient represents the first quantitative measure of resistance to flexion in the mouse model, and therefore provides a valuable tool for investigating flexor tendon scarring and adhesions in this mouse model.

The data, shown in FIG. 3C, suggest that significant adhesions, that limit the MTP joint flexion ROM, develop in either graft type. The adhesion coefficient 14 days post grafting was 29- and 26-fold greater than normal FDL tendon (n=8) for both auto- (n=12) and allografts (n=12), respectively (p<0.001). However, there was no significant difference between auto- and allograft adhesion coefficients at 14 days. At 28 days post grafting, the adhesion coefficient of the autografts (n=9) was 83-fold (p<0.001) greater that normal tendon (n=8). In contrast, the adhesion coefficient for freeze-dried allograft tendon (n=10) was increased 16-fold compared to normal tendon, and was 5-fold less than the adhesion coefficient measured in the autograft tendons (p<0.001).

By 42 days and thereafter, the adhesion coefficients were significantly decreased in both groups, but were higher than was observed in normal, un-operated FDL tendons. The MTP flexion ROM (MTP flexion is defined as the flexion angle upon the application of an excursion load of 19 g) was further measured. As shown in FIG. 3D, a significant negative correlation ($r^2=-0.95$; $p<0.0001$) between the empirically determined adhesion coefficient and the measured MTP flexion ROM was observed, validating the use of adhesion coefficient as a quantitative measure of resistance to flexion.

Interestingly, and as shown in FIGS. 3B and 3C, simply transplanting a graft and then evaluating the MTP joint flexion immediately after surgery (Day 0, n=9) revealed that the adhesion coefficient increased only 2-fold, as compared to normal FDL tendon ROM. Without being restricted to any one theory of operation, this could be a result of the suture interfering with the gliding of the FDL graft or skin tightening resulting from closure of the incision. However, these data suggest that the significant increases in the adhesion coefficient, and decreases in the MTP joint ROM in the autografts and allografts, seen at 14 and 28 days post transplantation, are likely attributable to excessive scarring during the repair process and are not simply a result of skin tightening (after incision closure) or the suture catching on the tarsal tunnel.

Following the flexion tests, the FDL tendons were isolated and released from the tarsal tunnel, and the foot severed at the metatarsals, leaving the tendon attached to the distal phalanges. After carefully dissecting remaining soft tissue adhering to the tendon using blunt tweezers, the harvested tendon was placed in sterile gauze soaked with saline to maintain adequate tissue hydration, and mechanically tested in tension until failure using previously published methods (Seiler et al., 1993; Seiler et al., 1997; Mikic et al., 2001; Chhabra et al., 2003). The tendons were re-hydrated at room temperature in a bath of PBS and then mechanically tested in tension until failure at a rate of 30 mm/per minute on an Instron 8841 DynaMight™ axial servo-hydraulic testing system (Instron Corporation, Norwood, Mass.), illustrated in FIG. 5A.

Briefly, each tendon was gripped between specially designed clamps to secure the phalanx and to grasp the proximal tendon end, which was sandwiched between two pieces of lab tape using a thin layer of cyanoacrylate, and directly clamped. The clamped tendon was then mounted on the testing system. After application of a 0.5 N preload, the tendon was loaded in tension in displacement control at a rate of 30 mm/minute until failure occurred. Force-displacement data were automatically logged and the biomechanical properties including the maximum tensile force and stiffness were determined.

Next, we investigated whether the non-destructive adhesion testing performed prior to the failure tensile tests had any effect on the measured tensile biomechanical properties. As shown in FIG. 4, the biomechanical properties of fresh autografts or freeze-dried allografts that were harvested 28 days post transplantation and tested for adhesions, were not significantly different from control specimens that were not tested for adhesions (n=5 per group, $p>0.05$).

Figure 5:
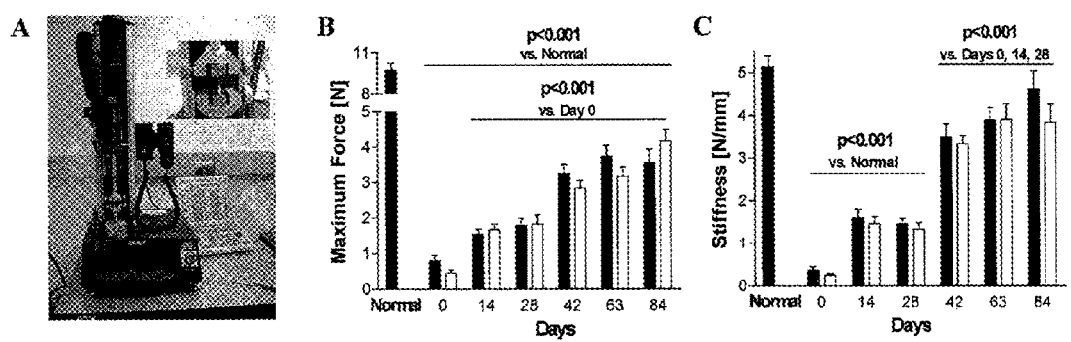
FIG. 5 illustrates an example of: (A) biomechanical testing of mouse FDL tendons on the Instron 8841 DynaMight™ Axial Servohydraulic Testing System; (B) maximum tensile force; and (C) stiffness; Autograft (black bars); freeze-dried allograft (white bars); (Mean±SEM).

Surprisingly, no significant differences in maximum tensile force or stiffness were observed between live autograft and freeze-dried allograft repairs at any time up to 84 days post-transplantation. While there were mild improvements over time in the tensile strength, as indicated by the maximum tensile force at failure, both autograft and allograft repairs remained less than 50% of the strength of normal FDL tendon, as shown in FIG. 5B. The stiffness for both the autograft and allograft repairs significantly increased over time, reaching 75-90% of the stiffness of normal un-operated FDL tendon, as shown in FIG. 5C. These results suggest that a freeze-dried allograft can perform as well as a fresh autograft.

Experiments testing live autograft and freeze-dried allograft repairs immediately after transplantation at day 0 were performed, the results of which are shown in FIGS. 5C and 5D. These tests measured the pull-out strength of the suture that anchors the graft to the host tendon ends. Values for average strength and stiffness of the Day 0 fresh autograft repair were 0.80 N±0.15 SEM, and 0.36 N/mm±0.08 SEM) respectively. Similarly, values for average strength and stiffness of the Day 0 freeze-dried allograft repair were 0.45 N±0.09 SEM, and 0.24 N/mm±0.04 SEM, respectively. These values are significantly lower than those observed for normal FDL tendon properties, and may be lower than the in vivo forces and excursions the FDL tendon may experience in the mouse model.

These results suggest the repair was protected from excessive in vivo loading that may have otherwise caused premature failure of the grafts and hinder healing by a proximal musculotendinous transection, unloading the FDL tendon. In addition to serving as protection against excessive early loading, the proximal musculotendinous transection can also serve to prevent tendon excursion, which likely further stimulates adhesion formation as previously demonstrated (Khan et al., 1996).

Figure 6:
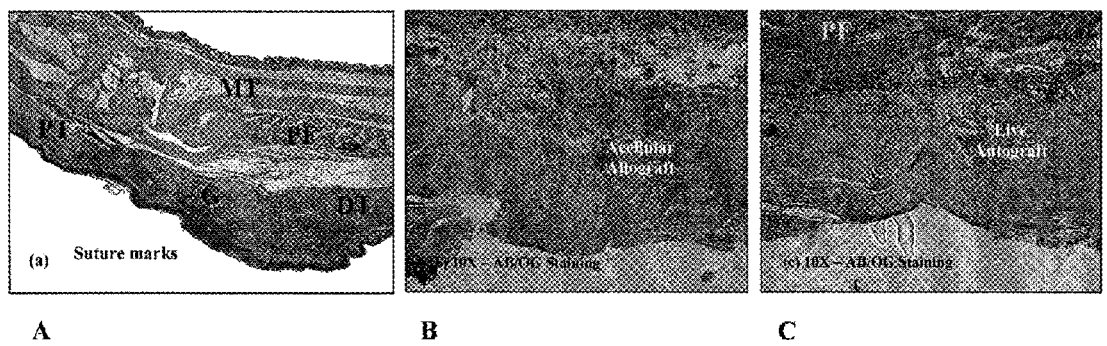
FIG. 6 illustrates an example of: (A) a representative en bloc Hemotoxylin & Eosin section (2× magnification) of an FDL allograft (G=graft, MT=metatarsal, PF=plantar fascia, PT=proximal FDL, DT=distal FDL); (B) a 7-day allograft repair with loose peripheral scarring (*); and (C) a 7-day autograft repair with dense peripheral scarring (*) causing adhesions to the PF and skin.

To understand the biological mechanisms involved in repair and adhesion of FDL tendon autografts and allografts, techniques were developed for en bloc embedding and histological processing of decalcified paws. This allowed examination of both the grafted repair and adhesions to the plantar fascia and the skin while the grafted tendon is in its anatomical location relative to adjacent structure. Results of these studies are shown in FIG. 6. This technique provides a significant improvement in that it preserves information about adhesions that would otherwise be lost if the graft tissue were dissected.

Example 2

Effects of Freeze-Drying on the Biomechanical Properties of FDL Tendon Grafts

To determine whether the process of freeze-drying adversely affects the biomechanical properties of the graft material prior to implantation, the tensile failure properties of fresh frozen and freeze-dried mouse FDL tendons were determined and compared.

Briefly, mouse FDL tendons were harvested as described earlier. Tendons were either tested freshly after harvest (fresh FDL tendon; Group 1), freshly frozen at −80° C. immediately after harvest (fresh-frozen FDL tendon, Group 2), freeze-dried once in a 2 L bench-top Labconco® lyophilizer (1× freeze-dried FDL tendon; Group 3), or freeze-dried, reconstituted in saline and then freeze-dried again (2× freeze-dried FDL tendon; Group 4). For testing, the tendons were re-hydrated at room temperature in a bath of PBS and then mechanically tested in tension until failure at a rate of 30 mm/minute as described above (Seiler et al., 1993; Seiler et al., 1997; Mikic et al., 2001; Chhabra et al., 2003).

Figure 7:
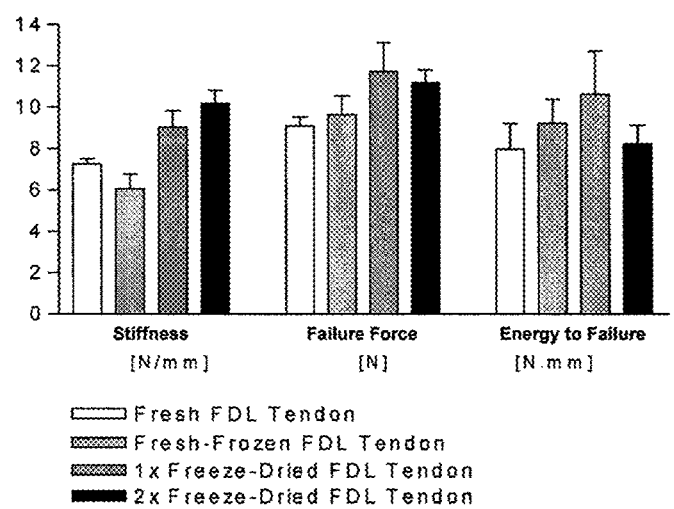
FIG. 7 illustrates the effects of freeze-drying on the mouse FDL tendon biomechanical properties.

Surprisingly, it was found that small, but statistically insignificant, improvements in the mechanical properties (failure force and stiffness) were observed in the freeze-dried tendon groups 3 and 4, as compared to the fresh and fresh-frozen tendon groups 1 and 2, respectively, as shown in FIG. 7. These findings suggest that freeze-drying tendons does not adversely affect the mechanical integrity of the graft.

Example 3

Figure 8:
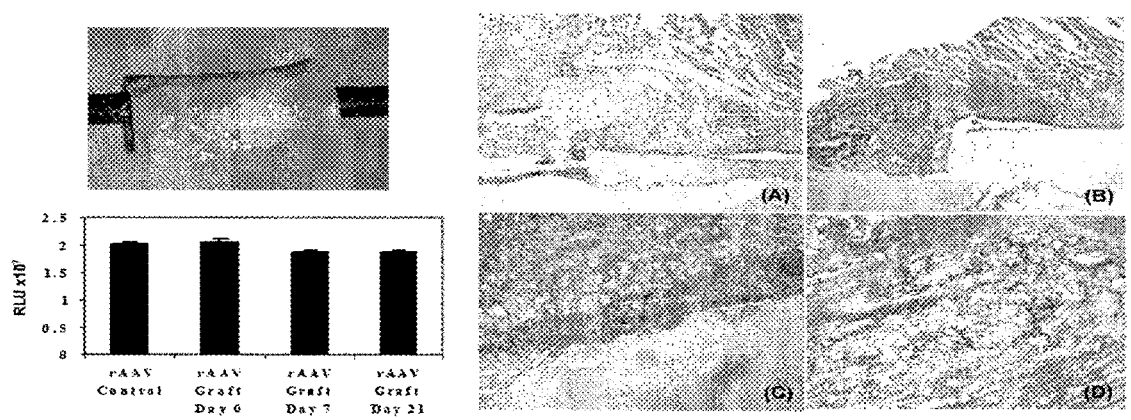
FIG. 8 illustrates an example of a rAAV-LacZ loaded freeze-dried bone graft stored for up to 21 days (top left). The bar graph (bottom left) demonstrates that rAAV can be freeze-dried onto allografts and stored without losing transduction efficiency. At right are 4 images representative of transduced cells (A-D).

Stability and Efficacy of the rAAV Targeted Gene Delivery in Revitalizing Bone Allografts About $10^8$ rAAV-LacZ units in 1 µL of virus solution were diluted in 50 µL of coating buffer containing 1% sorbitol in 0.1% buffered phosphate saline (PBS), and the mixture used to coat mouse femoral allografts, which in this example were 5 mm long. Once coated, the femoral allografts were freeze-dried. After freeze-drying and various storage times, the femoral allografts were incubated with HEK-293 cells. The infectivity of the virus upon re-hydration was verified by measuring the β-gal activity of the cultured 293 cells. As shown in FIG. 8, lyophilized rAAV preparations coated on femoral allografts preserve their infectivity, even after prolonged storage times (up to 21 days following coating).

The rAAV coated bone allografts were then used to repair segmental defects in mouse femurs. About $10^7$ infectious units of rAAV-LacZ were used to coat each allograft. Grafted femurs were harvested at days 14 and 28 and X-gal staining performed to examine the transducing efficiency of rAAV-LacZ. As demonstrated in FIG. 8 (micrographs in the right panel), a large number of cells in the proximity of allograft stained positive for β-galactosidase (β-gal) indicating the presence and expression of the rAAV-LacZ construct. β-gal positive cells were located within bone callus as well as along the shaft of allografts. These result demonstrate that freeze-dried rAAV remains viable and effective at infecting neighboring cells both in vitro and in vivo.

Figure 9:
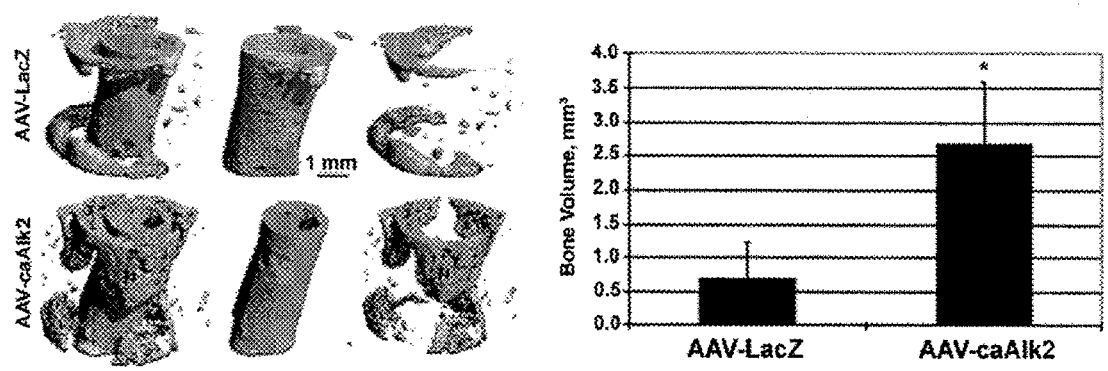
FIG. 9 illustrates an example of micro-CT imaging (left) of rAAV-coated allografts showing the bone that forms around the rAAV-caAlk2 coated allograft, and bone volume (right) produced as compared to the rAAV-LacZ controls.

To evaluate the efficacy of transferring BMP signals, for example a therapeutic agent, to the cortical surface of processed allografts, femoral allografts were coated with rAAV-caAlk2, a constitutively active form of the BMP receptor Alk2, and evaluated for their effect on healing in the mouse model for times, as compared to control allografts coated with rAAV-LacZ. To analyze the three-dimensional (3D) structure of these rAAV coated allografts, micro-CT analysis of the femurs harvested from the mice 6-weeks transplant was performed. The results, shown in FIG. 9, demonstrate that significant new bone formation can be induced by the rAAV-caAlk2 coating on the surface of the allograft. The data indicate that rAAV-based delivery can be an effective way in which to deliver therapeutically effective genes to aid in graft repair and remodeling.

Example 4 rAAV-Mediated Gene Transfer Via Freeze-Dried FDL Tendon Allografts

In vitro experiments were performed to determine the efficacy of loading freeze-dried tendon allografts with rAAV-LacZ. In these experiments, FDL tendon allografts (3 mm in length) were lyophilized, then soaked in 50 µL of PBS solution in a vial containing $5 \times 10^7$ particles of rAAV-LacZ. After allowing the dehydrated grafts to uptake the solution for 30 minutes, the grafts were snap-frozen and then freeze-dried again, a sample of which is shown in FIG. 10A.

The rAAV-loaded grafts were then individually placed in culture wells containing HEK-293 cells. As a positive control, 50 µL of the rAAV-LacZ was added directly into separate wells containing HEK-293 cells. As a negative control, freeze-dried FDL tendon allografts not coated with rAAV-LacZ were also placed in culture wells containing HEK 293 cells. All cultures were allowed to incubate for 48 hours, after which some wells were stained for β-gal activity using X-gal, to visualize transduced cells, while other wells were processed for spectrophotometric quantification of β-gal activity.

Figure 10:
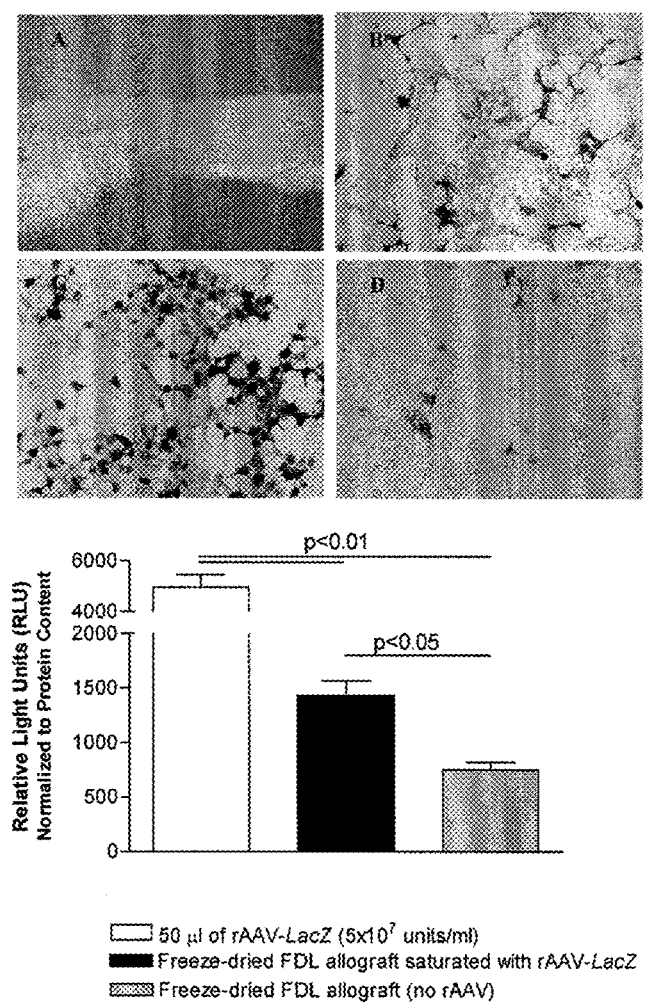
FIG. 10 illustrates an example of: (A) a freeze-dried FDL tendon allograft loaded with rAAV-LacZ; (B-D) random fields of LacZ expressing cells; and (E) quantitative measurement of β-gal activity by a Galacto-Light™ luminescence assay.

As shown in FIG. 10B-D, X-gal staining for β-gal activity showed that large numbers of cells were transduced after 48-hour incubation with the rAAV-LacZ loaded freeze-dried FDL allografts, whereas control cultures incubated with an uncoated FDL allograft were negative for β-gal activity. The pattern of β-gal expression suggests that transduction is influenced by diffusion of the virus as it is released from the allograft. As shown in FIG. 10E, β-gal activity, in cells transduced by a direct addition of 50 µL of the viral vector, was significantly higher than that of the rAAV/LacZ-loaded freeze-dried allografts. Similarly, β-gal activity in cells transduced with rAAV/LacZ-loaded freeze-dried FDL allografts was 2-fold higher than levels observed in negative controls.

These results suggest that the hydrophilic nature of the freeze-dried FDL tendon allografts result in adsorption of virus from the rAAV-containing solution. Furthermore, the adsorbed virus retains activity, even after freeze-drying. Thus, in some embodiments, variation in rAAV loading on the freeze-dried allograft is achieved by varying the concentration of the rAAV particles in solution used in the loading step. Viral load can also be varied, within limits, by the volume of virus-containing solution that is applied to the allograft. In some embodiments, both the concentration of virus in the loading solution, and the volume of loading solution applied to the allograft, can be varied.

To demonstrate the in vivo effectiveness of targeted delivery of recombinant adeno-associated viral (rAAV) vectors using the freeze-dried FDL tendon allograft as a delivery vehicle, freeze-dried FDL tendon allografts were loaded with rAAV-Luc (firefly luciferase reporter gene) as described above and then implanted in the left FDL tendon of 4 mice as described in Example 1. In addition, one mouse was directly injected intramuscularly with 50 µL of rAAV-Luc (about $5 \times 10^9$ particles) solution in the quadriceps of its right leg.

Figure 11:
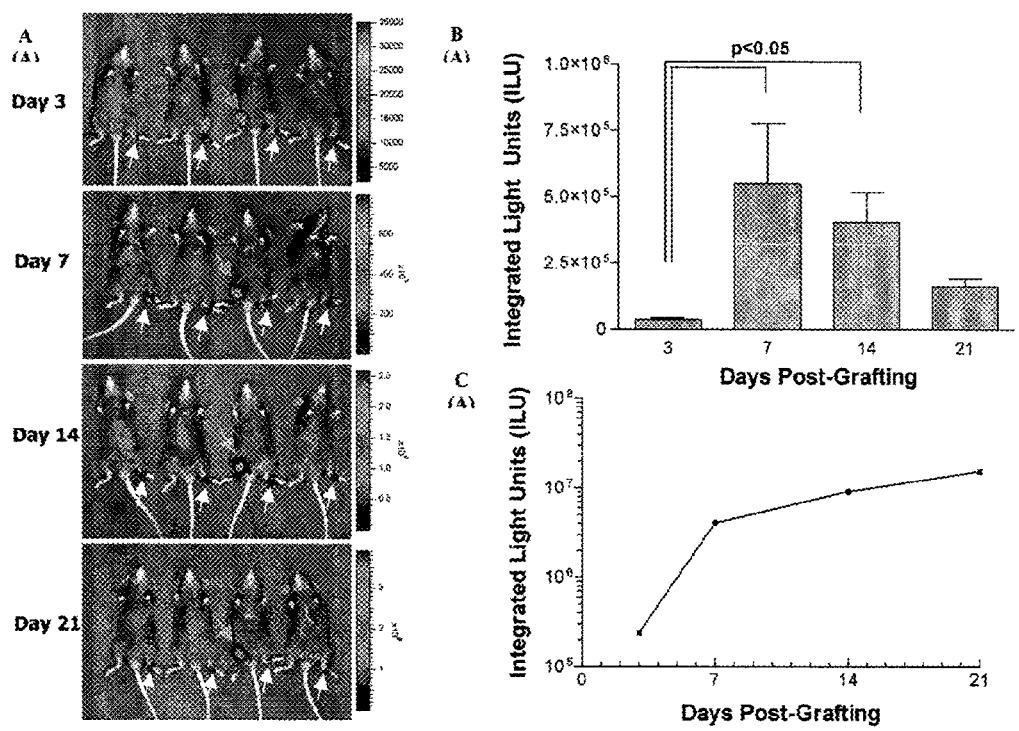
FIG. 11 illustrates an example of results of bioluminescence assays in experiments using rAAV-Luc coated allografts: (A) bioluminescence imagery of four mice. In each panel (day 3, 7, 14, and 21) the bottom four upward pointing arrows indicate sites of implantation of rAAV-Luc allografts; the downward directed arrow shows luminescence at the site of direct injection of rAAV-Luc into the quadriceps of a control mouse (third from left); (B) quantitation of bioluminescence from the graft ROI (region of implantation) of the same four mice; and (C) quantitation of the bioluminescence produced at the site of the direct injection of rAAV-Luc.

To assess transduction in vivo over time, the mice were imaged 3, 7, 14, and 21 days post grafting using a real-time bioluminescent imaging (BLI) system (IVIS® Imaging System, Xenogen Corp., Alameda, Calif.), as shown in FIG. 11. The system outputs data in the form of pseudo-color maps and/or graphically as measurements of integrated light units, as computed from measurements of total integrated light signal emitted from a standardized region of interest (ROI) in a standard time interval, for example, during a 3 min exposure. The results indicate that detectable bioluminescence can be localized to the targeted tissues, indicated by the arrows in FIG. 11A. The data also show that expression of luciferase in rAAV-loaded allografts was variable, peaking at 7 days following allograft implantation, and persisting at lower levels, up to 21 days. In contrast, direct muscle injection resulted in luciferase expression that continued to increase up to 21 days.

Figure 12:
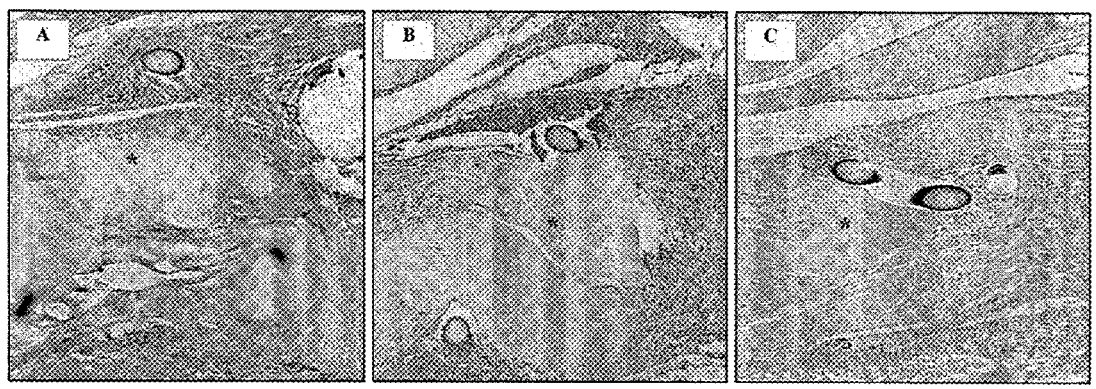
FIG. 12 illustrates exemplary immunohistochemical sections of one end of the rAAV-LacZ loaded allografts stained for β-gal activity at: (A) 7 days; (B) 14 days; and (C) negative control (2° antibody only).

To confirm that rAAV-loaded allografts mediate transient transduction of host cells, FDL tendon allografts were loaded with rAAV-LacZ and then implanted in the FDL tendons as allografts. The mice were sacrificed at 7 and 14 days after implantation, and the grafted tissues were harvested, fixed, paraffin-embedded, and processed for immunohistochemistry using an antisera specific to β-gal (PAb # GTX26646, GeneTex, Inc., San Antonio, Tex.). As shown in FIG. 12, host cells in the peripheral tissue were effectively transduced by the rAAV-LacZ vector, as evidenced by detectable β-gal expression. In addition, more intense expression was observed on day 7 as compared to day 14.

Example 5 rAAV-Mediated GDF5 Gene Delivery Accelerates Wound Healing In Vitro

A functionally verified rAAV-Gdf5 vector was prepared. Briefly, the cDNA for GDF5 was PCR amplified from the pSPORT-Gdf5 expression vector with primers containing 5' NotI and 3' EcoRI restriction sites to facilitate subcloning into the pSub201 rAAV transfer vector. pSub201 includes flanking inverted terminal repeats, a CMV promoter, and a portion of the 3' UTR from the BGHA gene. After ligation and transformation, positive clones propagated in *E. coli* were confirmed by restriction digest and DNA sequencing. The resulting plasmid (pAAV-Gdf5) was used to produce rAAV using a helper virus-free method and purified as previously described (Ito et al., 2005).

Figure 13:
FIG. 13 illustrates an example of an analysis of functionality of rAAV-Gdf5 vector. The top panel shows results of a PCR analysis of GDF5 mRNA expression in HEK-293 cells; (lane 1) pUC19 control vector; (lane 2) pSPORT-Gdf5; (lane 3) pAAV-Gdf5; Lane 4 is a PCR product positive control sample derived by amplification of pSPORT-Gdf5. The bottom panel shows results of a Western blot analysis of GDF5 expression; Lanes 1-3 contained protein from cells transfected with rAAV-LacZ; Lanes 4-6 contained protein from cells transfected with rAAV-Gdf5; Lane 7 is a positive control and contained 10 ng of purified GDF5 protein.
Figure 13:

HEK-293 cells were grown in 6-well plates and transfected with pUC19, pSPORT-Gdf5, or pAAV-Gdf5. Forty-eight hours after transfection cells were lysed, total mRNA harvested, reverse transcribed, and a region of interest amplified by PCR. The results shown in FIG. 13 (upper panel) show the expected 485 bp PCR product. HEK-293 cells were also grown in 6-well plates and infected with varying amounts of rAAV-LacZ or rAAV-Gdf5. After 48 hrs, culture supernatants were collected and 30 µL samples were processed for Western blot analysis using a GDF5-specific antisera, and a chemiluminescence detection system. Autoradiography of the chemiluminescent signal from the Western blot revealed in a dose-dependent manner the predicted 13.7 kDa GDF5 protein, as shown in FIG. 13 (lower panel).

Figure 14:
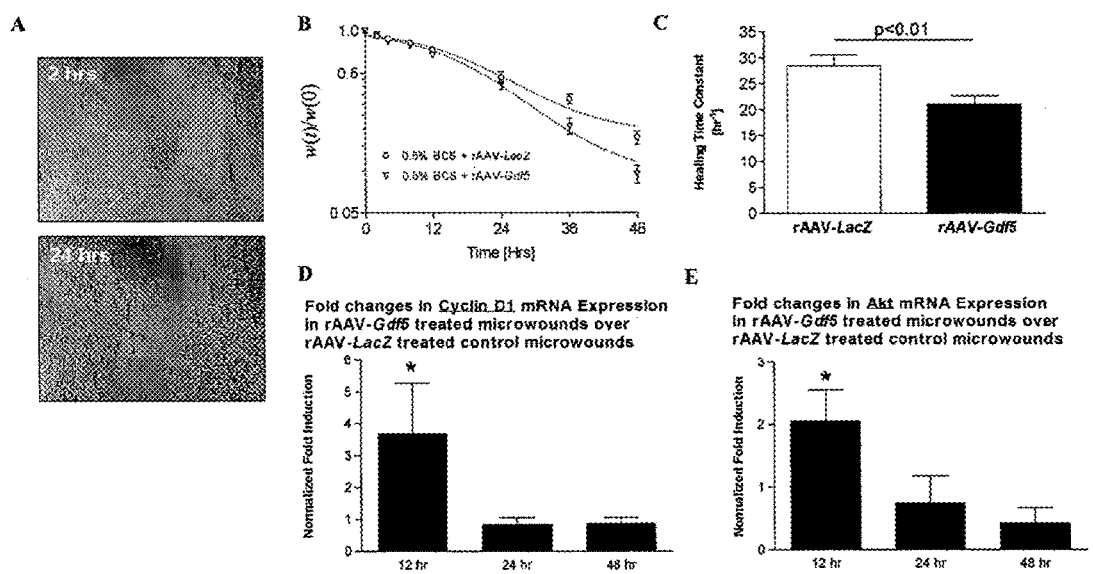
FIG. 14 illustrates exemplary results of microwound experiments: (A) micrographs of cells at 2 hrs and 24 hrs after wounding; (B) normalized wound width 48 hours after treatments; (C) healing time constants for different treatments; (D) changes in cyclin D1 mRNA expression in rAAV-Gdf5 treated microwound cells; and (E) changes in Akt mRNA expression in rAAV-Gdf5 treated microwound cells.

The functionality of rAAV-Gdf5 gene delivery was evaluated in vitro using a micro wound monolayer assay. Briefly, mouse embryonic fibroblast (NIH3T3) cells were plated and allowed to grow to 80% confluence. The cells were then serum deprived for 24 hours prior to creating wounds. A pipettor tip was scratched across the monolayer, resulting in wounds initially measuring 1.00±0.20 mm. Cells were then cultured in the presence of 0.5% bovine calf serum (BCS) and $5.0 \times 10^7$ particle units per mL of either rAAV-LacZ or rAAV-Gdf5. Photographs of micro wounds were taken at 0, 2, 4, 8, 12, 24, 36, and 48 hours, an example of which is shown in FIG. 14A. Using a custom Matlab program, the average width of each wound was measured at each time and normalized by the initial wound width ($w(t)/w(0)$). The data were fitted to the equation:

$$w(t)/w(0) = A/(B \cdot \exp(t/\tau) + 1).$$

where $\tau$ represents the healing time constant. Thus, faster healing wounds have a lower healing time constant. The results of these experiments, shown in FIGS. 14B and 14C demonstrate that infecting 3T3 cells with rAAV-Gdf5 leads to accelerated wound healing, as indicated by the significantly lower healing time constants. Data shown in FIG. 21 demonstrates that healing time constant is reduced in a dose dependent manner by increasing levels of GDF5 protein.

As shown in FIGS. 14D and 14E, real-time PCR analysis indicated that the accelerated microwound healing rates are associated with early induction of cyclin D1 and Akt (a regulatory protein for β1-integrin recycling and cell motility) mRNA expression, suggesting that rAAV-Gdf5 produces effects on both cell proliferation and migration. The data also suggest that transducing the 3T3 cells with rAAV-Gdf5 leads to accelerated wound closure, correlated with increased cellular proliferation and migration.

Example 6

Figure 15:
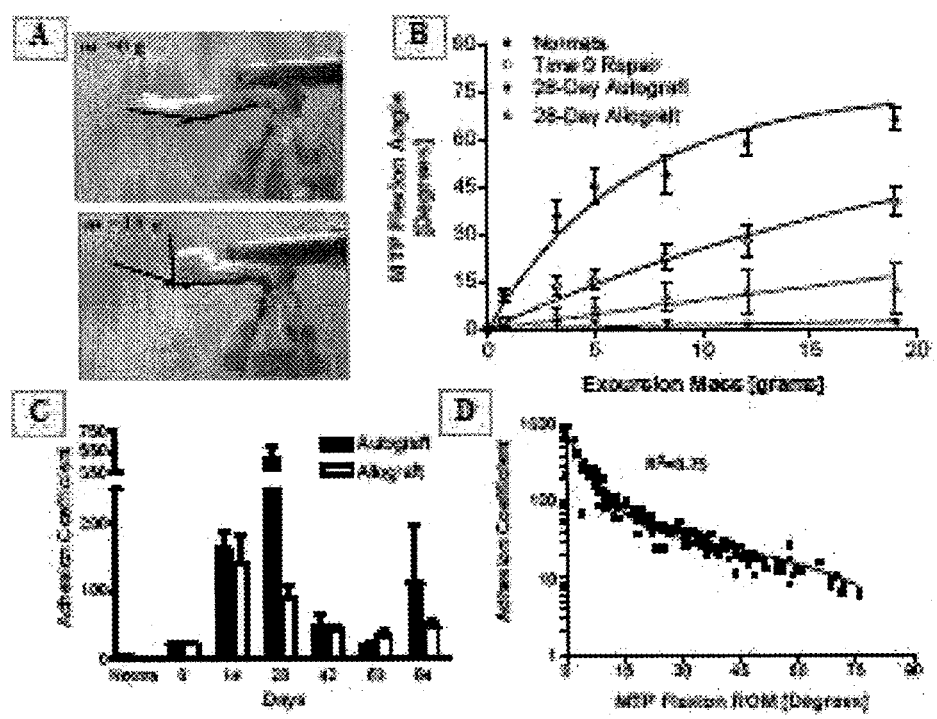
FIG. 15 illustrates an example of biomechanical testing for adhesion formation: (A) experimental setup for testing MTP joint flexion range of motion (ROM); (B) MTP flexion angle; (C) adhesion coefficient; and (D) adhesion coefficient versus MTP flexion ROM.

Murine FDL Tendon Grafts Experience Persistent Adhesions up to 84 Days Post Grafting Differences in the biomechanical properties between autograft and allograft FDL tendon repair, beyond 28 and 42 days, and up to 84 days (12 weeks) post grafting, were studied. The data, shown in FIG. 15, indicate that significant adhesions, which limit the metatarsophalangeal (MTP) joint flexion range of motion (ROM), evident by higher than normal tendon adhesion coefficients, developed in both graft types. The adhesion coefficient 14 days post grafting was 29- and 26-fold greater than normal FDL tendon (n=8) for both auto- (n=12) and allografts (n=12; p<0.001). There was no significant difference between auto- and allograft adhesion coefficients at 14 days. At 28 days post grafting, the adhesion coefficient of the autografts (n=9) was 83-fold (p<0.001) greater that normal tendon (n=8).

Figure 16:
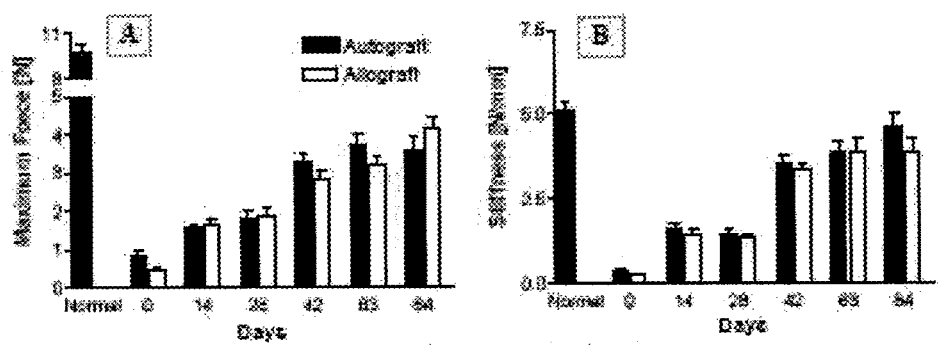
FIG. 16 illustrates examples of: (A) maximum tensile force; and (B) stiffness measurements in live autograft and freeze-dried allograft repairs.

In contrast, the adhesion coefficient for freeze-dried allograft tendon (n=10) was increased 16-fold compared to normal tendon, and was 5-fold less than the adhesion coefficient measured in the autograft tendons (p<0.05). By 42 days, and thereafter, adhesion coefficients decreased significantly in both groups, but remained higher than normal un-operated FDL tendons. FIG. 16 illustrates results of breaking tensile force (left panel) and linear tensile stiffness (right panel) measurements in allografts and autografts, at times up to 84 days post-operatively.

Example 7

The ROSA26 Isograft Model as a Tool to Assess Cellular and Molecular Contributions of Donor Tissue To investigate the contribution of cellular subpopulations in the graft (such as epitenon and endotenon cells), and populations of cells from the host (macrophages, fibroblasts, and endothelial vascular cells), to the onset of adhesions, live isografts were transplanted from ROSA26 (LacZ transgenic) mice into 3 mm gap defects in the distal FDL of syngeneic non-transgenic littermates (n=4). The grafted tendons were harvested at 14 and 21 days (n=2 each) and consecutive serial cross-sections were prepared for histomorphometric analysis using X-gal staining to detect β-gal activity, or immunohistochemistry with an anti-PCNA antisera.

Figure 17:
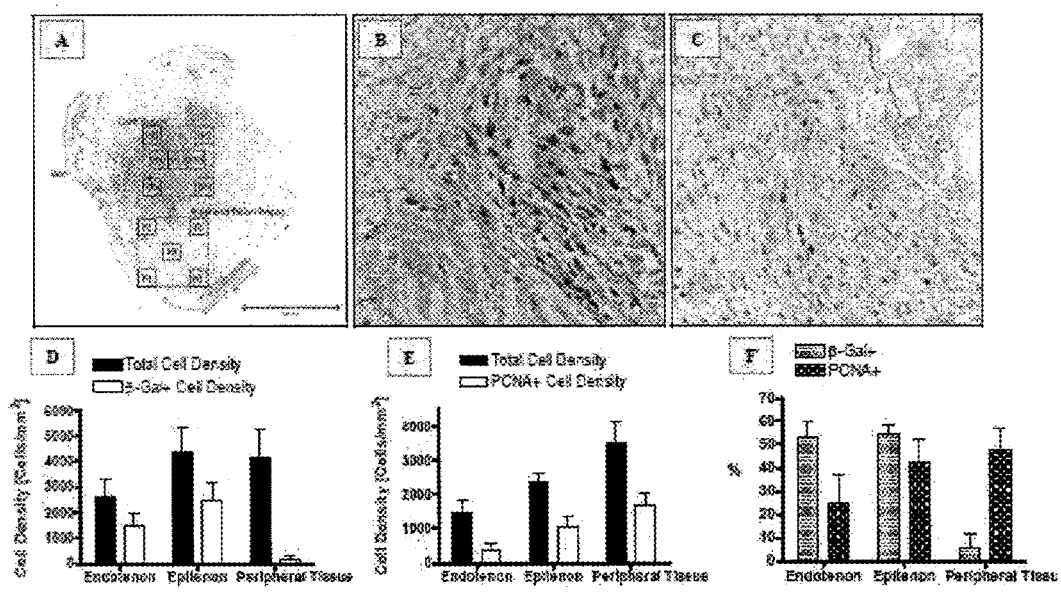
FIG. 17 illustrates an example of histomorphometric analysis of ROSA26 FDL tendon isograft, 14 days post transplantation. (A) A 3 μm cross-section stained with X-gal and nuclear fast red showing a grid for identifying the sampling fields; (B) representative section (40×) of X-gal stained cells in the graft region; (C) representative section (40×) of cells stained with anti-PCNA; (D) total cell density and cell density of β-gal positive cells; (E) total cell density and cells density of PCNA positive cells; and (F) percentage of cells that are β-gal positive or PCNA positive.

FIG. 17A demonstrates result obtained using a histomorphometric sampling algorithm to analyze a 3 µm cross-section of the graft and peripheral tissue. The graft was identified and approximately outlined based upon the blue staining (β-gal+) of the donor cells. Two sampling fields, indicated by large boxes in FIG. 17A, were selected in the Graft Region and Peripheral Tissue Region and digitally imaged. Smaller fields in the endotenon (EN1, 2, and 3) and the epitenon (EP1, 2, 3, and 4), as well as peripheral granulation tissue (P1, 2, 3, 4, and 5), were then imaged for histomorphometry. Images of the corresponding sampling fields from PCNA stained slides were also taken. The frequency (%) of β-gal positive cells, and PCNA positive cells, in each of the sampling regions was determined by two independent analysts. The results are shown in FIG. 17D-F.

The results from the 14-day sample suggests increased cellularity in the graft region, especially in the epitenon, as a result of donor cell proliferation (i.e., cells that are β-gal positive and PCNA positive), and host cell proliferation and infiltration (i.e., cells that are PCNA positive and β-gal negative). The data also suggest high proliferation activity of host cells (PCNA positive), and a limited contribution of donor cells (β-gal positive), in the peripheral (adhesion) tissue. The data demonstrate the utility and power of this histomorphometric approach in delineating the cellular and molecular events during the pathogenesis of adhesion following graft transplantation.

Example 8 rAAV-Mediated Gene Transfer Via Freeze-Dried FDL Tendon Allografts is Transient and Localized Experiments were designed to make use of freeze-dried FDL tendon allografts as a delivery vehicle for recombinant adeno-associated viral (rAAV) vectors expressing a GDF5 gene. Two experiments using reporter genes were performed. In the first experiment, FDL tendon allografts (3 mm in length) were freeze-dried, then soaked in 50 µL of PBS solution containing about $5 \times 10^9$ particles of rAAV-Luc. After 30 minutes, the grafts were snap-frozen and then freeze-dried again. The freeze-dried rAAV-Luc loaded allografts were then implanted in the left FDL tendons of 4 mice. In addition, one mouse was directly injected intramuscularly with 50 µL of the rAAV-Luc solution in the hamstring of its right leg. To assess transduction in vivo over time, the mice were imaged on days 3, 7, 14, and 21 post grafting using a real-time bioluminescent imaging (BLI) system (IVIS® Imaging System, Xenogen Corp., Alameda, Calif.). The maps shown in FIG. 11A represent light intensity computed from measurements of total integrated light signal emitted from a standardized region of interest (ROI), during a standard time interval (3 min exposure), and corrected by subtracting background emissions.

FIG. 11 (Left Panel) shows the in vivo BLI detection of the rAAV-Luc transduced host cells over time. The detected bioluminescence was localized to the targeted tissues, shown by arrows in FIG. 11A. The data indicate that transduction by rAAV-loaded allografts is transient, with luciferase expression peaking after 7 days, and persisting at lower levels at 21 days. In contrast, direct muscle injection resulted in luciferase expression that continued to increase over time. In the second experiment, FDL tendon allografts were loaded with rAAV-LacZ as described above and then implanted in the FDL tendons as allografts. The mice were sacrificed at 7 and 14 days and the grafted tissues harvested, fixed, paraffin embedded, and processed for immunohistochemical staining to detect β-galactosidase expressed by the LacZ gene (PAb # GTX26646, GeneTex, Inc., San Antonio, Tex.). As shown in FIG. 12, host cells in the peripheral tissue were transduced by the rAAV-LacZ vector, with β-galactosidase detectable at 7 and 14 days.

Figure 18:
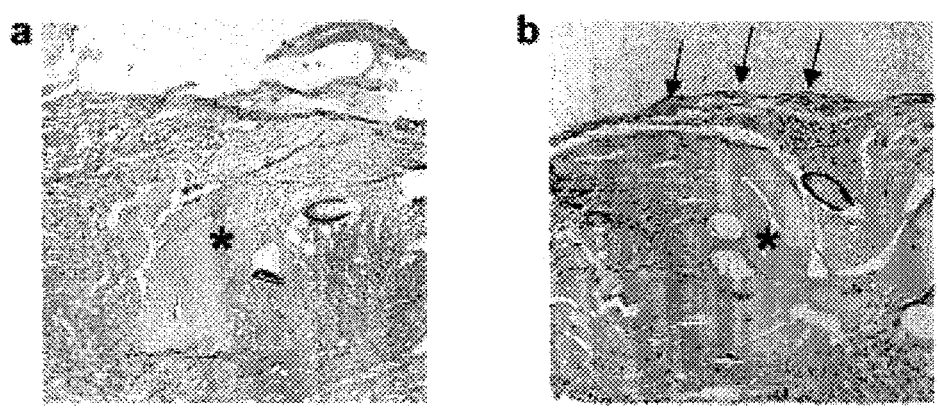
FIG. 18 illustrates an example of immunohistochemical analysis of GDF5 expression in cells. (A) Control sample transduced with rAAV-LacZ; (B) area of expression by cells transduced with rAAV-Gdf5 and stained with anti-GDF5 antibody (arrows).

Example 9 rAAV-GDF5 Loaded FDL Tendon Allograft Transduce Host Cells—Immunohistochemistry Evidence Additional experiments demonstrated that a tendon allograft, associated with a rAAV-GDF5 GDF5 expression vector, produced according to the methods disclosed in the previous examples, is able to induce host cells resulting in expression of GDF5 protein. FIG. 18 shows data from experiments where a tendon allograft associated with either rAAV-lacZ or rAAV-GDF5 had been transplanted, and at 14 days post-grating tissue was removed and processed for immunohistochemistry.

As shown in FIG. 18A, cells transduced with the rAAV-lacZ control construct showed no ectopic expression of GDF5. As shown in FIG. 18B, cells transduced with rAAV-GDF5 displayed detectable levels of GDF5 synthesized by host cells (shown by arrows) at the periphery of the allograft (shown by the asterisk).

Figure 19:
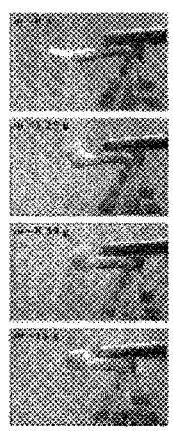
FIG. 19 illustrates exemplary results of experiments showing improved gliding characteristics and reduced adhesions in processed FDL tendon allografts: (A) Photograph of experimental set-up; (B) MTP flexion vs. excursion mass in rAAV-LacZ and rAAV-Gdf5 treated samples; (C) adhesion coefficient data; and (D) maximum MTP flexion angle data.
Figure 19:
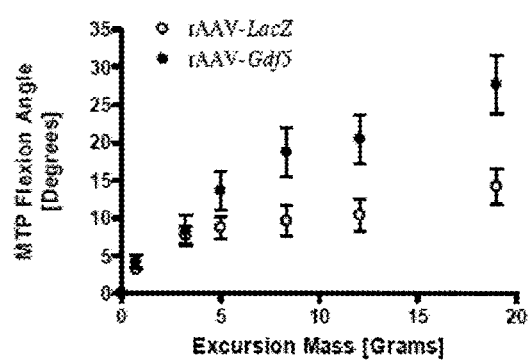
Figure 19:
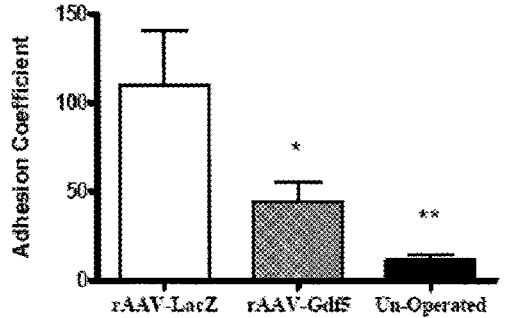
Figure 19:
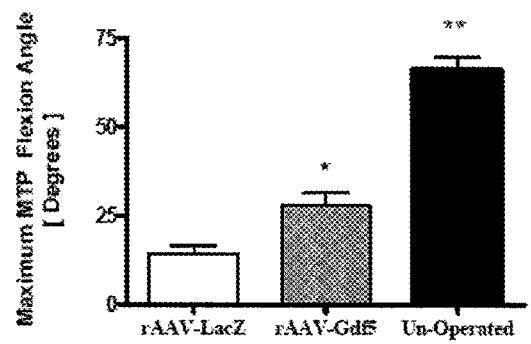
Figure 20:
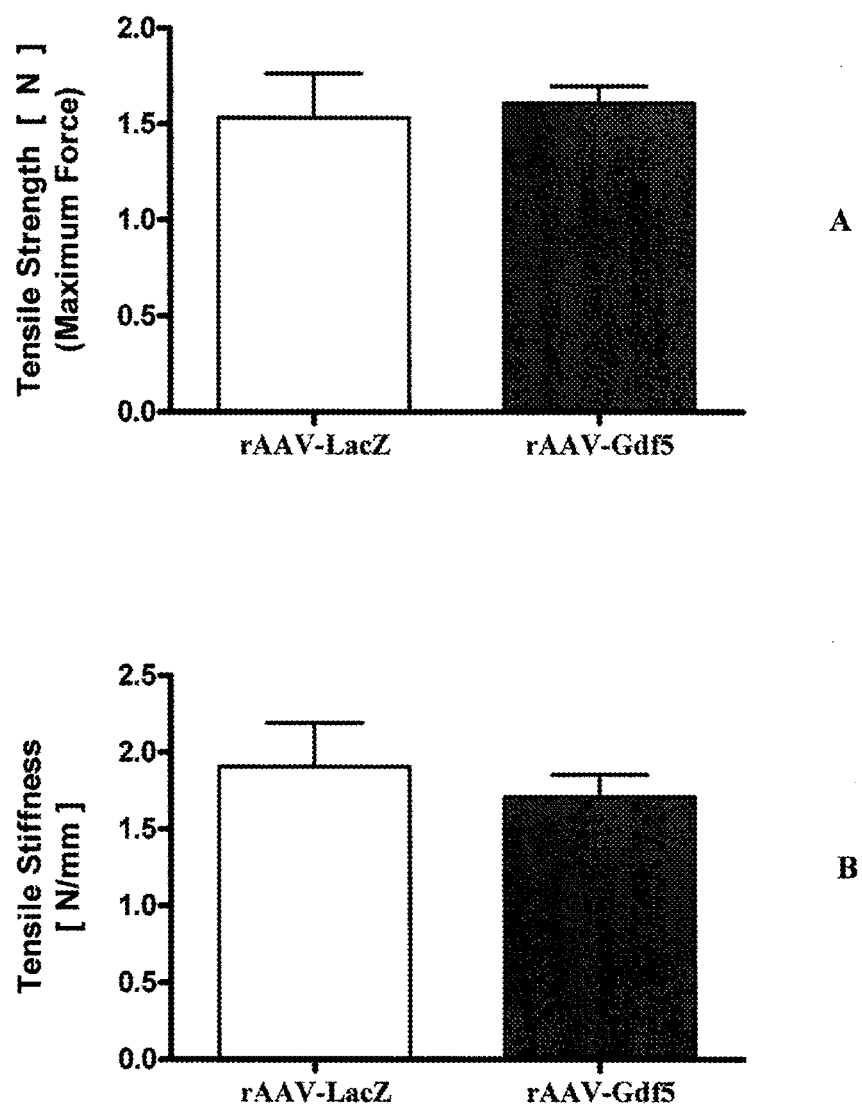
FIG. 20 illustrate exemplary results of experiments showing that treatment of allografts with rAAV-Gdf5 does not affect biomechanical properties of processed FDL tendon allografts: (A) Tensile strength vs. treatment; and (B) tensile stiffness vs. treatment.

Example 10 rAAV-GDF5 Improves Gliding Characteristics and Reduces Adhesions in Processed FDL Tendon Allografts In other experiments, it was found that a tendon allograft associated with rAAV-Gdf5 GDF5 expression vector, made according to the methods disclosed in the previous examples, was able to improve joint function, and reduce the number of adhesions associated with a prior surgery. As shown in FIG. 19B, compared to control rAAV-lacZ, transduction with rAAV-Gdf5 was associated with a significantly reduce MTP flexion angle over increasing weight at 14 days post surgery. Moreover, compared to rAAV-lacZ, transduction with rAAV-Gdf5 was associated with reduction in adhesion coefficient, as shown in FIG. 19C. Adhesion coefficients in experimental samples were about half that of control samples. Finally, as compared to rAAV-lacZ, transduction with rAAV-Gdf5 was associated with a significantly larger maximum MTP flexion angle, as shown in FIG. 19D. Data from a control experiment, illustrated in FIG. 20, shows that transduction with rAAV-Gdf5 had no effect on FDL tensile properties. As such, the improved gliding characteristics and reduced adhesions are associated with GDF5 expression, as opposed to altered FDL tensile properties.

Example 11

Effect of GDF-5 Protein Dosage on Healing Time Constant

Figure 21:
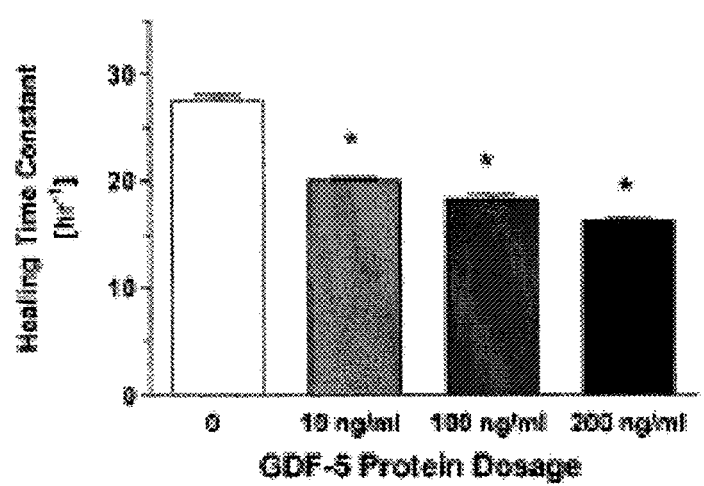
FIG. 21 illustrates the relationship between healing time constant and GDF5 protein dosage.

In an experiment to test the effect of GDF-5 protein dosage on the healing time constant, 3T3 cells were grown to about 80% confluence and then micro-wounded as described above. Cells were then treated with 0.5% bovine calf serum and incremental doses of rmGDF5 protein. As shown in FIG. 21, increasing the concentration of GDF5 in the culture medium was correlated with a reduction in healing time constant, indicating that GDF5 accelerates healing in a dose-dependent manner.

Example 12

Effect of GDF5 Expression on Flexion Range and Gliding

Figure 22:
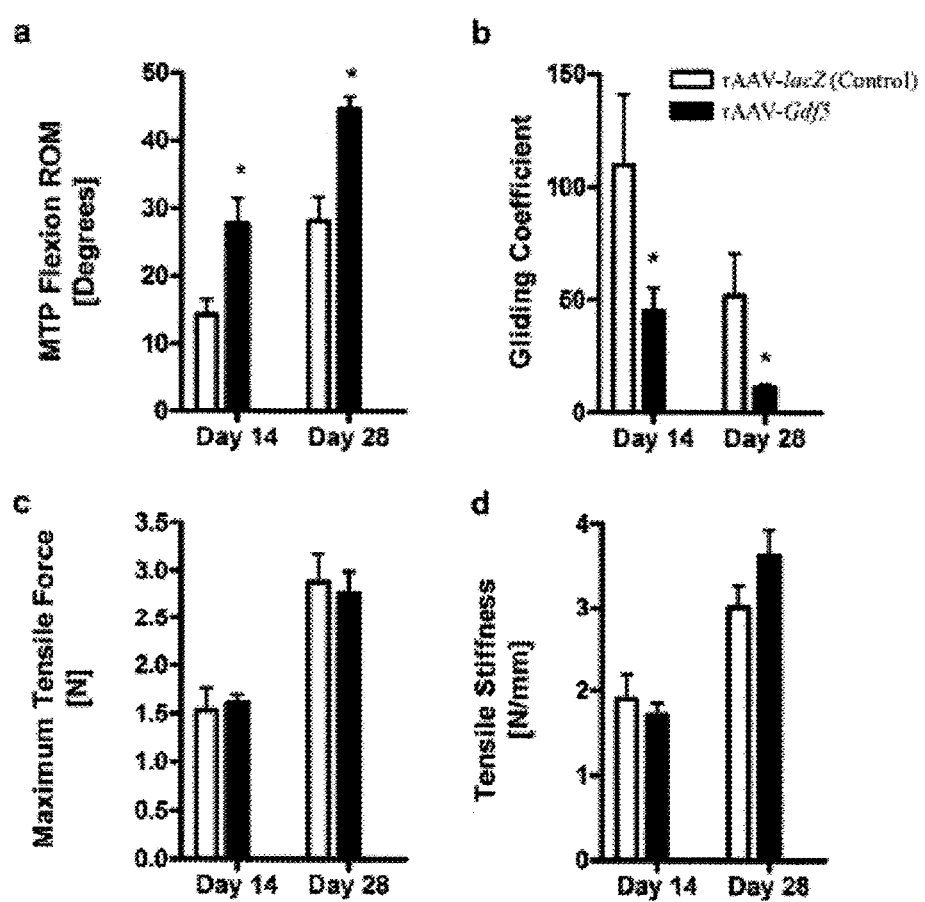
FIG. 22 illustrates the effect of GDF5 expression on: (A) flexion ROM; (B) gliding coefficient; (C) maximum tensile force; and (D) tensile stiffness, 14 and 28 days post-operatively.

In FIG. 22 are provided results of experiments to further evaluate the functional contributions of GDF5 expression to healing of reconstructed FDL tendons. Mice had their FDL tendons reconstructed with freeze-dried allografts loaded with rAAV-LacZ or rAAV-Gdf5. Animals were sacrificed at 14 or 28 days post-operatively (n=9 per treatment time), tissue harvested, and subjected to the MTP flexion test to determine the MTP joint flexion ROM (FIG. 22A); or gliding coefficient (FIG. 22B). Tendons were then isolated and tested to determine their breaking tensile force (FIG. 22C), and their linear tensile stiffness (FIG. 22D). Errors shown in FIG. 21 are standard errors of the mean.

MTP flexion testing showed that rAAV-Gdf5 loaded allografts display significantly improved range of joint flexion as compared to allografts loaded with the rAAV-LacZ control vector. Gliding coefficient was decreased in the rAAV-Gdf5 sample, and gliding function improved relative to control samples. While stiffness appeared greater in rAAV-Gdf5 samples at 28 days, the data were not statistically significant in this example.

Example 13

Effect of GDF5 Expression on Cell Repopulation and Tissue Remodeling

Figure 23:
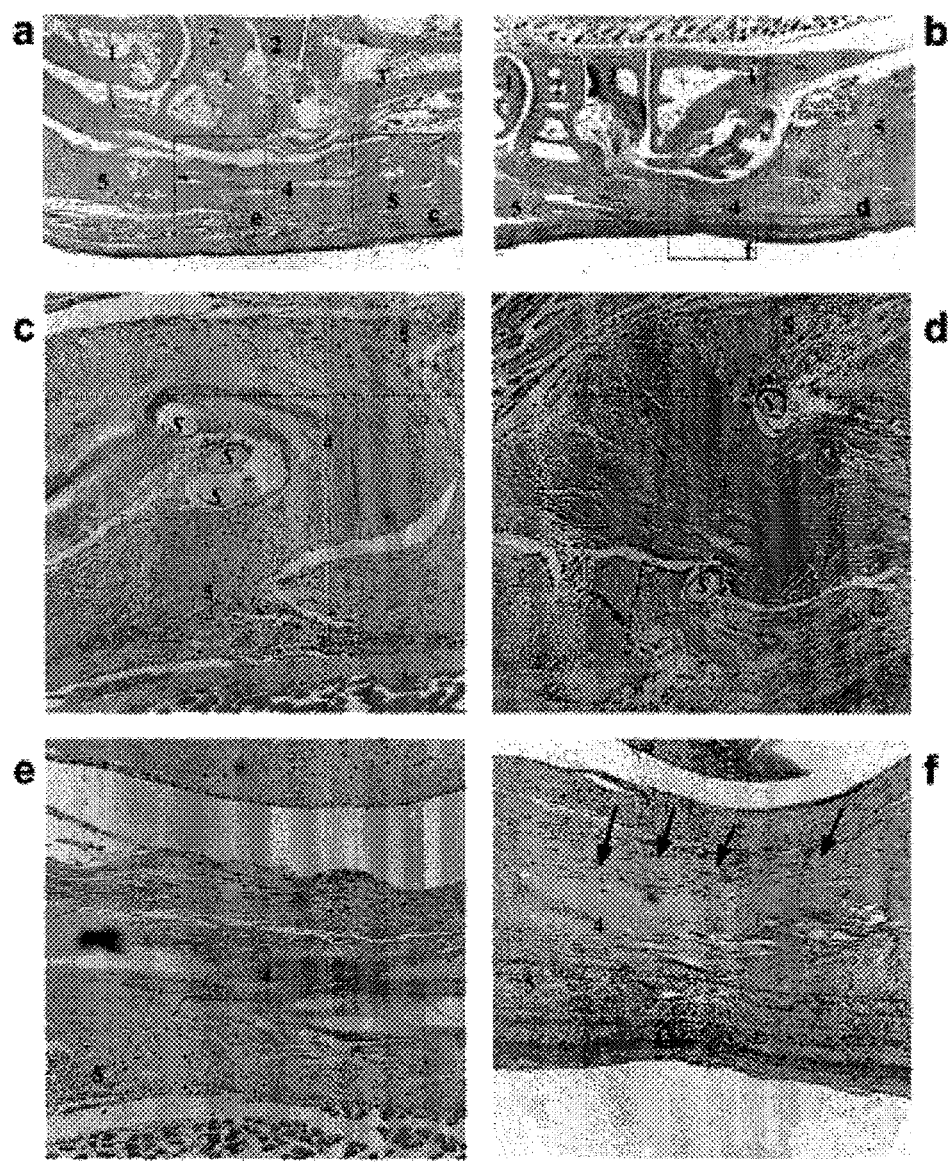
FIG. 23 illustrates data showing that rAAV-Gdf5 loading of allografts mediates cell re-population and remodeling of fibrotic scar tissue: (A,C,E) rAAV-LacZ loaded allografts; (B,D,F) rAAV-Gdf5 loaded allografts. Tissues marked by numbers are (1) talus; (2) tarsal bone; (3) metatarsal bone; (4) FDL tendon allograft; and (5) fibrotic/inflammatory tissue. (S) remnants of sutures. The arrows in (f) indicate a remodeled tissue aligned with a rAAV-Gdf5 allograft.

Histological analysis was performed to determine whether GDF5 expression provided any advantages with respect to cell repopulation or tissue remodeling. Sample of FDL tendon allografts were taken 14 days post-operatively, processed and stained with Alcian Blue and Orange G. Micrographs at 4× (FIGS. 23A and B) show the implanted grafts with their anatomical relationships to the surrounding tissue. Boxed regions are shown in the 20× magnified regions shown in FIG. 23 C-F.

Wherein the rAAV-LacZ control allograft was mostly acellular and surrounded with disorganized and hypercellular fibrotic tissue (FIG. 23E), the rAAV-Gdf5 treated graft was surrounded by organized tissue that resembles neotendon and integrates with the graft, and appears to have been repopulated by cells (FIG. 23F).

APPLICABILITY OF DISCLOSED EMBODIMENTS

Figure 24:
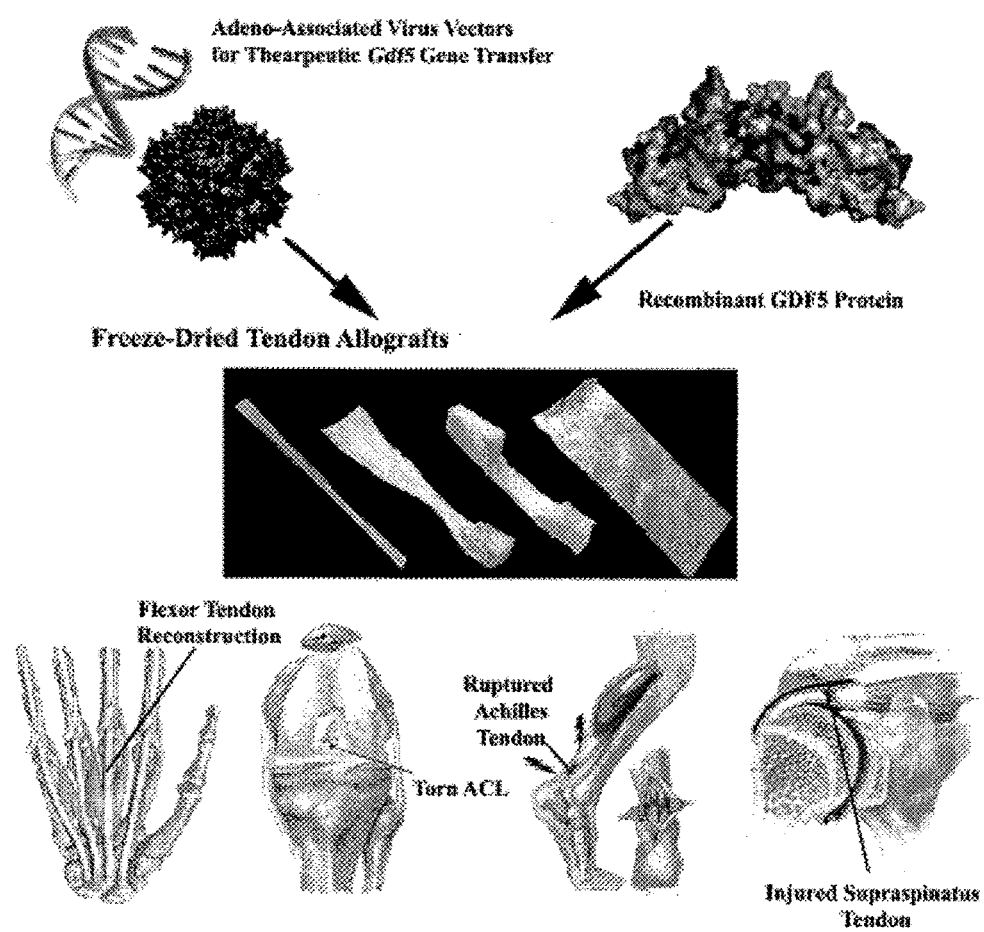
FIG. 24 illustrates some applications of some embodiments of the present disclosure for repair of soft tissue injuries.

As illustrated in FIG. 24, embodiments as described herein have broader use beyond those described in the exemplary embodiments. For example, and without being limiting, embodiments of the compositions and methods described herein can be used generally to improve the repair and/or healing of tissue in the body. For example, in some embodiments, compositions and methods to repair tendon can be applied for use in repair of rotator cuff, Achilles tendon, flexor and extensor tendons of the hands and feet, as well as frequently reconstructed ligaments such as the anterior or posterior cruciate ligaments.

Further, a variety of materials are suitable for use in providing a matrix material. For example, and without being limiting, materials useful to provide allograft scaffolds can include musculoskeletal tissues including cartilage (for chondral and osteo-chondral grafts), meniscus, and intervertebral disc tissues. In some embodiments, allografts can comprise material combined from more than one source. For example, an allograft comprising bone-tendon-bone can be useful in addressing challenging clinical problems such as the need to insert soft tissue into bone.

In addition, in some embodiments, GDF5 protein can be loaded onto an allograft matrix in the form of a pharmaceutical composition. Here, the composition can be designed to release GDF5 at a desired rate such that a sustained increase in local concentration to levels effective to promote tissue healing and/or remodeling.

Thus, as described herein, embodiments of the present disclosure are useful to provide a simplified tissue engineering system in which freeze-dried allograft tissue can be used to deliver cues to host cells resident at a site of injury, such that programming of the repair response occurs. Freeze-dried allografts provide a number of additional advantages including, but not limited to, indefinite shelf life prior to use, biomechanical properties similar or equal to fresh or fresh frozen tissue, reduced immunogenicity, and the ability to be remodeled during healing. In addition, freeze-dried allografts have native hydrophilic properties that permit efficient reconstitution of tissue in physiologic solutions that include therapeutic agents.

The skilled artisan will recognize the interchangeability of various features from different embodiments. Similarly, the various features and steps discussed above, as well as other known equivalents for each such feature or step, can be mixed and matched by one of ordinary skill in this art to perform compositions or methods in accordance with principles described herein. Although the disclosure has been provided in the context of certain embodiments and examples, it will be understood by those skilled in the art that the disclosure extends beyond the specifically described embodiments to other alternative embodiments and/or uses and obvious modifications and equivalents thereof. Accordingly, the disclosure is not intended to be limited by the specific disclosures of embodiments herein.

LIST OF REFERENCES

Abrahamsson, S. O., Gelberman, R. H., Amiel, D., Winterton, P. & Harwood, F. (1995) *J. Orthop. Res.* 13: 58-66.

Abrahamsson, S. O. & Lohmander, S. (1996) *J. Orthop. Res.* 14: 370-6.

Ark, J. W., Gelberman, R. H., Abrahamsson, S. O., Seiler, J. G., 3rd & Amiel, D. (1994) *J. Hand. Surg. [Am]* 19: 249-58.

Asencio, G., Abihaidar, G. & Leonardi, C. (1996) *J. Hand Surg. [Br]* 21: 84-8.

Aspenberg, P. & Forslund, C. (1999) *Acta. Orthop. Scand.* 70: 51-4.

Awad, H. A., Boivin, G. P., Dressler, M. R., Smith, F. N., Young, R. G. & Butler, D. L. (2003) *J. Orthop. Res.* 21: 420-31.

Awad, H. A., Butler, D. L., Boivin, G. P., Smith, F. N., Malaviya, P., Huibregtse, B. & Caplan, A. I. (1999) *Tiss. Eng.* 5: 267-77.

Banes, A. J., Tsuzaki, M., Hu, P., Brigman, B., Brown, T., Almekinders, L., Lawrence, W. T. & Fischer, T. (1995) *J. Biomech.* 28: 1505-13.

Bechtold, J. E., Eastlund, D. T., Butts, M. K., Lagerborg, D. F. & Kyle, R. F. (1994) *Am. J. Sports Med.* 22: 562-6.

Beris, A. E., Darlis, N. A., Korompilias, A. V., Vekris, M. D., Mitsionis, G. I. & Soucacos, P. N. (2003) *J. Hand Surg. [Am]* 28: 652-60.

Bowden, B. W. (1974) *J. Am. Osteo. Ass'n* 74: 144-7.

Bright, R. W. & Green, W. T.: (1981) *J. Pediatr. Orthop.* 1: 13-22.

Bunnell, S. (1953) *Ind. Med. Surg.* 22: 251-4.

Chang, J., Thunder, R., Most, D., Longaker, M. T. & Lineaweaver, W. C.: (2000) *Plast. Reconstr. Surg.* 105: 148-55.

Chen, Y., Luk, K. D., Cheung, K. M., Xu, R., Lin, M. C., Lu, W. W., Leong, J. C. & Kung, H. F.: (2003) *Gene Ther.* 10: 1345-53.

Chhabra, A., Tsou, D., Clark, R. T., Gaschen, V., Hunziker, E. B. & Mikic, B. (2003) *J. Orthop. Res.* 21: 826-35.

Chow, S. P., Hooper, G. & Chan, C. W. (1983) *Hand* 15: 136-42.

Clark, R. T., Johnson, T. L., Schalet, B. J., Davis, L., Gaschen, V., Hunziker, E. B., Oldberg, A. & Mikic, B. (2001) *Connect. Tissue Res.* 42: 175-86.

Cole, D. W., Ginn, T. A., Chen, G. J., Smith, B. P., Curl, W. W., Martin, D. F. & Poehling, G. G. (2005) *Arthro.* 21: 786-90.

Coyle, M. P., Jr., Leddy, T. P. & Leddy, J. P. (2002) *J. Hand Surg. [Am]* 27: 581-5.

Duffy, F. J., Seiler, J. G., Hergrueter, C. A., Kandel, J. & Gelberman, R. H. (1992) *J. Hand Surg. [Br]* 17: 275-7.

Eming, S. A., Krieg, T. & Davidson, J. M. (2004) *Expert Opin. Biol. Ther.* 4: 1373-86.

Gelberman, R. H. & Manske, P. R. (1985) *Hand Clin.* 1: 35-42.

Gelberman, R. H., Seiler, J. G., 3rd, Rosenberg, A. E., Heyman, P. & Amiel, D. (1992) *Scand J. Plast. Reconstr. Surg Hand Surg.* 26: 257-64.

Gerich, T. G., Kang, R., Fu, F. H., Robbins, P. D. & Evans, C. H. (1996) *Gene Ther.* 3: 1089-93.

Gerich, T. G., Kang, R., Fu, F. H., Robbins, P. D. & Evans, C. H. (1997a) *Knee Surg. Sports Traumatol. Arthrosc.* 5: 118-23.

Gerich, T. G., Lobenhoffer, H. P., Fu, F. H., Robbins, P. D. & Evans, C. H. (1997b) *Unfallchirurg.* 100: 354-62.

Grieger, & Samulski, R. J. (2005) *Adv. Bioch. Eng. Biotechnol.* 99: 119-145.

Hsu, C. & Chang, J. (2004) *J. Hand Surg. [Am]* 29: 551-63.

Indelicato, P. A., Bittar, E. S., Prevot, T. J., Woods, G. A., Branch, T. P. & Huegel, M. (1990) *Am. J. of Sports Med.* 18: 335-42.

Ito, H., Koefoed, M., Tiyapatanaputi, P., Gromov, K., Goater, J. J., Carmouche, J., Zhang, X., Rubery, P. T., Rabinowitz, J., Samulski, R. J., Nakamura, T., Soballe, K., O'Keefe, R. J., Boyce, B. F. & Schwarz, E. M. (2005) *Nat'l Med.* 11: 291-7.

Jackson, D. W., Grood, E. S., Goldstein, J. D., Rosen, M. A., Kurzweil, P. R., Cummings, J. F. & Simon, T. M. (1993) *Am. J. of Sports Med* 21: 176-85.

Jackson, D. W., Halbrecht, J., Proctor, C., Van Sickle, D. & Simon, T. M. (1996) *J. Orthop. Res.* 14: 255-64.

Jackson, D. W., Windler, G. E. & Simon, T. M. (1990) *Am. J. Sports Med.* 18: 1-10; discussion 10-1.

Jorgensen, H. G., McLellan, S. D., Crossan, J. F. & Curtis, A. S. (2005) *Cyto.* 30: 195-202.

Kashiwagi, K., Mochizuki, Y., Yasunaga, Y., Ishida, O., Deie, M. & Ochi, M. (2004) *Scand. J. Plast. Reconstr. Surg. Hand Surg.* 38: 193-7.

Khan, U., Edwards, J. C. & McGrouther, D. A. (1996) *J. Hand Surg. [Br]* 21: 813-20.

Khan, U., Kakar, S., Akali, A., Bentley, G. & McGrouther, D. A. (2000) *J. Bone Joint Surg. Br.* 82: 1054-8.

Koefoed, M., Ito, H., Gromov, K., Reynolds, D. G., Awad, H. A., Rubery, P. T., Ulrich-Vinther, M., Soballe, K., Guldberg, R. E., Lin, A. S., O'Keefe, R. J., Zhang, X. & Schwarz, E. M. (2005) *Mol. Ther.* 12: 212-8.

Leddy, J. P. (1988) Operative Hand Surgery, 2nd ed., Green, D. P. ed., pp. 1935-1968.

Lee, S. J., & Nathans, D. (1988) *J. Biol. Chem.* 263: 3521-3527.

Leversedge, F. J., Zelouf, D., Williams, C., Gelberman, R. H. & Seiler, J. G., 3rd (2000) *J. Hand. Surg. [Am]* 25: 721-30.

Lindsay, W. K., Thomson, H. G. & Walker, F. G.: (1960) *Br. J. Plast. Surg.* 3: 1-9.

Lister, G. (1985) *Hand Clin.* 1: 133-46.

Liu, T. K. & Yang, R. S. (1997) *J. Trauma* 43: 103-6.

Lou, J., Tu, Y., Burns, M., Silva, M. J. & Manske, P. (2001) *J. Orthop. Res.* 19: 1199-202.

Lundborg, G. (1976) *Hand* 8: 235-8.

Lundborg, G., Hansson, H. A., Rank, F. & Rydevik, B. (1980) *J. Hand Surg. [Am]* 5: 451-61.

Lundborg, G. & Rank, F. (1978) *J. Hand Surg. [Am]* 3: 21-31.

Lundborg, G. & Rank, F. (1980) *Hand* 12: 3-11.

Lundborg, G., Rank, F. & Heinau, B. (1985) *Scand J. Plast. Reconstr. Surg.* 19: 113-7.

Manske, P. R., Gelberman, R. H. & Lesker, P. A. (1985a) *Hand Clin.* 1: 25-34.

Manske, P. R., Gelberman, R. H., Vande Berg, J. S. & Lesker, P. A. (1984) *J. Bone Jt. Surg. [Am]* 66: 385-96

Manske, P. R., Lesker, P. A., Gelberman, R. H. & Rucinsky, T. E. (1985b) *J. Hand Surg. [Am]* 10: 632-7.

Masada, K., Yasuda, M., Hashimoto, H. & Nakai, K. (2002) *Scand. J. Plast. Reconstr. Surg. Hand. Surg.* 36: 243-4.

Mehta, V., Kang, Q., Luo, J., He, T. C., Haydon, R. C. & Mass, D. P. (2005) *J. Hand Surg. [Am]* 30: 136-41.

Mikic, B. (2004) *Ann. Biomed. Eng.* 32: 466-76.

Mikic, B., Bierwert, L. & Tsou, D. (2006) *J. Orthop. Res.* 24: 831-41.

Mikic, B., Schalet, B. J., Clark, R. T., Gaschen, V. & Hunziker, E. B. (2001) *J. Orthop. Res.* 19: 365-71.

Morotome, Y., Goseki-Sone, M., Ishikawa, I. & Oida, S. (1998) *Biochem. Biophys. Res. Commun.* 244: 85-90.

Morrison, W. A. & Cleland, H. (1995) *Ann. Acad. Med. Sing.* 24: 26-31.

Naam, N. H. (1997) *J. Hand Surg. [Am]* 22: 323-7.

Nakamura, T., Yamamoto, M., Tamura, M. & Izumi, Y. (2003) *J. Perio. Res.* 38: 597-605.

Nasca, R. J. (1988) *Clin. Orthop. & Rel. Res.* 228: 218-26.

Potenza, A. D. & Herte, M. C. (1982) *J. Hand Surg. [Am]* 7: 196-9.

Praemer, A., Furner, S. & Rice, D. (1999) *Musculoskeletal Conditions in the United States.* American Academy of Orthopedic Surgeons.

Ramesh, R., Kumar, N., Sharma, A. K., Maiti, S. K., Kumar, S. & Charan, K. (2003a) *J. Vet. Med—Ser.* A 50: 520-6.

Ramesh, R., Kumar, N., Sharma, A. K., Maiti, S. K. & Singh, G. R. (2003b) *J. Vet. Med.—Ser.* A 50: 511-9.

Rickert, M., Jung, M., Adiyaman, M., Richter, W. & Simank, H. G. (2001) *Growth Fact.* 19: 115-26.

Rickert, M., Wang, H., Wieloch, P., Lorenz, H., Steck, E., Sabo, D. & Richter, W. (2005) *Connect. Tiss. Res.* 46: 175-83.

Roberts, T. S., Drez, D., Jr., McCarthy, W. & Paine, R.: [erratum appears in (1991) *Am. J. Sports Med.* May-June; 19(3): 272]. (1991) *Am. J. of Sports Med.* 19: 35-41.

Sakellarides, H. T. & Papadopoulos, G. (1996) *J. Hand Surg. [Br]* 21: 63-6.

Schneider, L. H. (1985) *Hand Clin.* 1: 109-20.

Schneider, L. H. & Hunter, J. M. (1988). Operative hand Surgery, Vol. 3, 2nd ed., Green D. P. ed., pp. 1969-2044, New York: Churchill Livingstone.

Seiler, J. G., 3rd, Chu, C. R., Amiel, D., Woo, S. L. & Gelberman, R. H. (1997) *Clin. Orthop. Relat. Res.* 345: 239-47.

Seiler, J. G., 3rd, Gelberman, R. H., Williams, C. S., Woo, S. L., Dickersin, G. R., Sofranko, R., Chu, C. R. & Rosenberg, A. E. (1993) *J. Bone Jt. Surg. [Am]* 75: 1004-14.

Seemann, P., Schwappacher, R., Kjaer, K. W., Krakow, D., Lehmann, K., Dawson, K., Stricker, S., Pohl, J., Ploger, F., Staub, E., Nickel, J., Sebald, W., Knaus, P., & Mundlos, S. (2005) *J. Clin. Invest.* 115: 2373-2381.

Sena, K., Morotome, Y., Baba, O., Terashima, T., Takano, Y. & Ishikawa, I. (2003) *J. Dent. Res.* 82: 166-71.

Singer, D. I., Morrison, W. A., Gumley, G. J., O'Brien, B. M., Mitchell, G. M., Barton, R. M. & Frykman, G. K. (1989) *J. Hand Surg. [Am]* 14: 55-63.

Slade, J. F., Bhargava, M., Barrie, K. A., Shenbagamurthi, D. & Wolfe, S. W. (2001) *J. Hand Surg. [Am]* 26: 813-20.

Smith, P., Jones, M. & Grobbelaar, A. (2004) *Scand. J. Plast. Reconstr. Surg. Hand Surg.* 38: 220-7.

Soslowsky, L. J., Thomopoulos, S., Tun, S., Flanagan, C. L., Keefer, C. C., Mastaw, J. & Carpenter, J. E. (2000) *J. Shoul. Elb. Surg.* 9: 79-84.

Stark, H. H., Anderson, D. R., Zemel, N. P., Boyes, J. H., Ashworth, C. R. & Rickard, T. A. (1989) *Clin. Orthop. Relat. Res.* 242: 51-9.

Tang, J. B., Zhang, Q. G. & Ishii, S. (1993) *J. Hand Surg. [Br]* 18: 31-2.

Taras, J. S. & Kaufmann, R. A. (2005) *Operative Hand Surgery,* 5th ed., Green, D. P. ed., pp. 241-276.

Taras, J. S. & Lamb, M. J. (1999) *J. Hand Ther.* 12: 141-8.

Tolat, A. R. & Stanley, J. K. (1993) *J. Hand Surg. [Br]* 18: 239-40.

Toritsuka, Y., Shino, K., Horibe, S., Nakamura, N., Matsumoto, N. & Ochi, T. (1997) *J. Orthop. Res.* 15: 294-300.

Valenti, P. & Gilbert, A. (2000) *Hand Clin.* 16: 573-8, viii.

Vermeylen, J. & Monballiu, G. (1991) *J. Hand Surg. [Br]* 16: 185-6.

Wainer, R. A., Clarke, T. J. & Poehling, G. G. (1988) *Arthro.* 4: 199-205.

Webster, D. A. & Werner, F. W. (1983a) *Clin. Orthop. & Rel. Res.* 238-43.

Webster, D. A. & Werner, F. W. (1983b) *Clin. Orthop. & Rel. Res.* 301-9.

Wehbe, M. A., Mawr, B., Hunter, J. M., Schneider, L. H. & Goodwyn, B. L. (1986) *J. Bone Jt. Surg. [Am]* 68: 752-63.

Wojciak, B. & Crossan, J. F. (1993) *Clin. Exp. Immunol.* 93: 108-14.

Wolfman, N. M., Hattersley, G., Cox, K., Celeste, A. J., Nelson, R., Yamaji, N., Dube, J. L., DiBlasio-Smith, E., Nove, J., Song, J. J., Wozney, J. M. & Rosen, V. (1997) *J. Clin. Invest.* 100: 321-30.

Wu, Y., Hu, Y. & Cui, S. (2000) *Chin. J. Traumata* 3: 34-38.

What is claimed is:

1. A surgical graft, for use in promoting healing of a diseased or injured tendon, comprising:
    an acellular, lyophilized, biologically derived matrix comprising a collagen; and
    at least one therapeutic agent, releasably coupled to the matrix and comprising an expression system, the expression system configured to result in expression of at least one therapeutic protein;
    wherein the graft is sized and shaped to be placed in a patient's body cavity in proximity to a diseased or injured tendon;
    wherein, when the graft is placed in the body cavity, the at least one therapeutic agent is released into the tendon;
    wherein the at least one therapeutic agent is in an amount effective to promote healing of the tendon and to reduce an amount of fibrotic adhesion of the tendon relative to a tendon that has been treated with a graft that does not include the therapeutic agent; and
    wherein the expression system comprises a recombinant adeno-associated virus carrying a nucleic acid having the sequence of SEQ ID NO: 1.

2. The graft of claim 1, wherein the healing comprises at least one of tissue remodeling, accelerating wound healing, or enhancing cell repopulation.

3. The graft of claim 1, wherein the healing comprises at least one of improving joint flexion, improving joint range of motion, or improving tendon gliding.

4. The graft of claim 1, wherein the collagen is derived from at least one of tendon or ligament.

5. The graft of claim 1, wherein the at least one therapeutic agent is adsorbed to the matrix.

6. The graft of claim 1, wherein the at least one therapeutic agent is sustained released.

7. A surgical graft, for use in promoting healing of a diseased or injured tendon, comprising:
    an acellular, lyophilized, biologically derived matrix comprising a collagen; and
    at least one therapeutic agent, releasably coupled to the matrix and comprising an expression system, the expression system configured to result in expression of at least one therapeutic protein;
    wherein the graft is sized and shaped to be placed in a patient's body cavity in proximity to a diseased or injured tendon;
    wherein, when the graft is placed in the body cavity, the at least one therapeutic agent is released into the tendon;
    wherein the at least one therapeutic agent is in an amount effective to promote healing of the tendon and to reduce an amount of fibrotic adhesion of the tendon relative to a tendon that has been treated with a graft that does not include the therapeutic agent; and
    wherein the expression system comprises a recombinant adeno-associated virus carrying a nucleic acid encoding a protein having the amino acid sequence of SEQ ID NO: 2.

8. The graft of claim 7, wherein the healing comprises at least one of tissue remodeling, accelerating wound healing, or enhancing cell repopulation.

9. The graft of claim 7, wherein the healing comprises at least one of improving joint flexion, improving joint range of motion, or improving tendon gliding.

10. The graft of claim 7, wherein the collagen is derived from at least one of tendon or ligament.

11. The graft of claim 7, wherein the at least one therapeutic agent is adsorbed to the matrix.

12. The graft of claim 7, wherein the at least one therapeutic agent is sustained released.

* * * * *